(12) United States Patent
Matsushita et al.

(10) Patent No.: US 10,501,718 B2
(45) Date of Patent: Dec. 10, 2019

(54) OBSERVATION APPARATUS

(71) Applicant: OLYMPUS CORPORATION, Tokyo (JP)

(72) Inventors: Akira Matsushita, Tokyo (JP); Shintaro Takahashi, Tokyo (JP); Masaru Mizunaka, Tokyo (JP); Shinichi Takimoto, Tokyo (JP); Tadashi Hirata, Tokyo (JP); Yohei Tanikawa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/848,623

(22) Filed: Dec. 20, 2017

(65) Prior Publication Data
US 2018/0179487 A1 Jun. 28, 2018

(30) Foreign Application Priority Data

Dec. 27, 2016 (JP) .................................. 2016-252699

(51) Int. Cl.
| | |
|---|---|
| *C12M 1/34* | (2006.01) |
| *G01J 5/10* | (2006.01) |
| *H04N 5/33* | (2006.01) |
| *H04N 5/225* | (2006.01) |
| *G01J 5/00* | (2006.01) |

(52) U.S. Cl.
CPC ........... *C12M 41/46* (2013.01); *G01J 5/0003* (2013.01); *G01J 5/10* (2013.01); *H04N 5/2252* (2013.01); *H04N 5/2256* (2013.01); *H04N 5/33* (2013.01); *G01J 2005/0077* (2013.01)

(58) Field of Classification Search
CPC ....................................................... C12M 41/46
USPC ........................................................ 435/288.7
See application file for complete search history.

(56) References Cited

U.S. PATENT DOCUMENTS

| | | | | |
|---|---|---|---|---|
| 2004/0115101 A1* | 6/2004 | Malin | ..................... | C12M 23/50 422/430 |
| 2005/0248836 A1* | 11/2005 | Tsuchiya | ............. | G01N 21/0332 359/368 |
| 2009/0082219 A1* | 3/2009 | Ermantraut | ........... | B01L 3/5027 506/10 |
| 2009/0141345 A1* | 6/2009 | Tsuchiya | ................. | B01L 9/523 359/393 |
| 2010/0009335 A1* | 1/2010 | Joseph | ................... | C12N 23/12 435/3 |

(Continued)

FOREIGN PATENT DOCUMENTS

JP 2003021628 1/2003

*Primary Examiner* — Kevin Joyner
*Assistant Examiner* — Holly M Mull
(74) *Attorney, Agent, or Firm* — Scully, Scott, Murphy & Presser, P.C.

(57) ABSTRACT

Provided is an observation apparatus including: a housing that has, in a top face thereof, a transmission window on which a container accommodating cells can be placed and through which light can pass; a camera portion that is accommodated in the housing and that captures observation light coming from the cells irradiated with illumination light emitted from an illumination portion and entering the housing by passing through a bottom face of the container and the transmission window of the housing; and a housing-interior heating portion that is accommodated in the housing and that heats the cells.

19 Claims, 17 Drawing Sheets

(56) References Cited

U.S. PATENT DOCUMENTS

| | | | | |
|---|---|---|---|---|
| 2011/0071681 A1* | 3/2011 | Liu | ............................ | B01L 7/52 |
| | | | | 700/269 |
| 2011/0134516 A1* | 6/2011 | Araya | ................. | G02B 21/0004 |
| | | | | 359/371 |
| 2014/0377880 A1* | 12/2014 | Emburgh | ................... | B01L 3/04 |
| | | | | 436/175 |

* cited by examiner

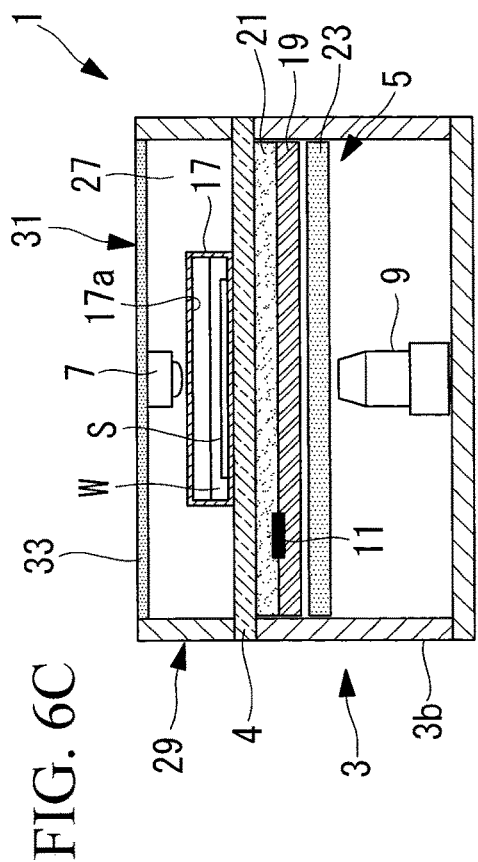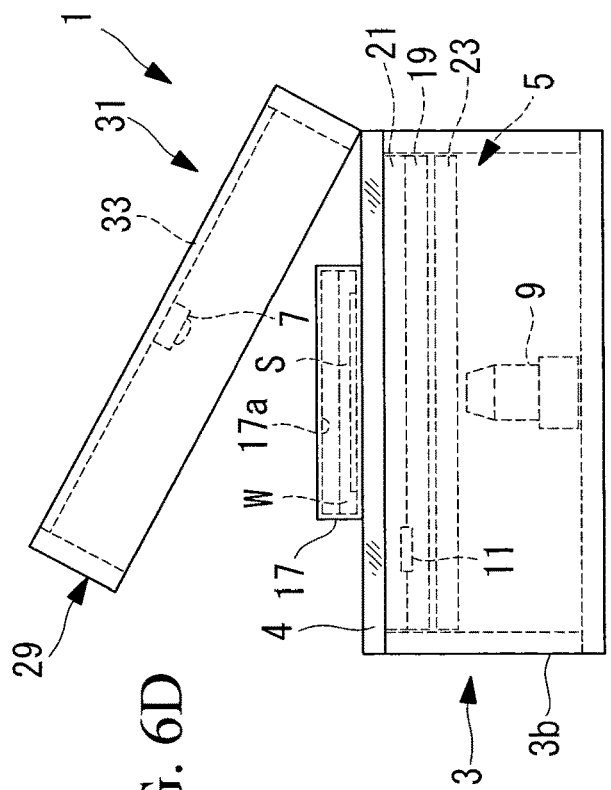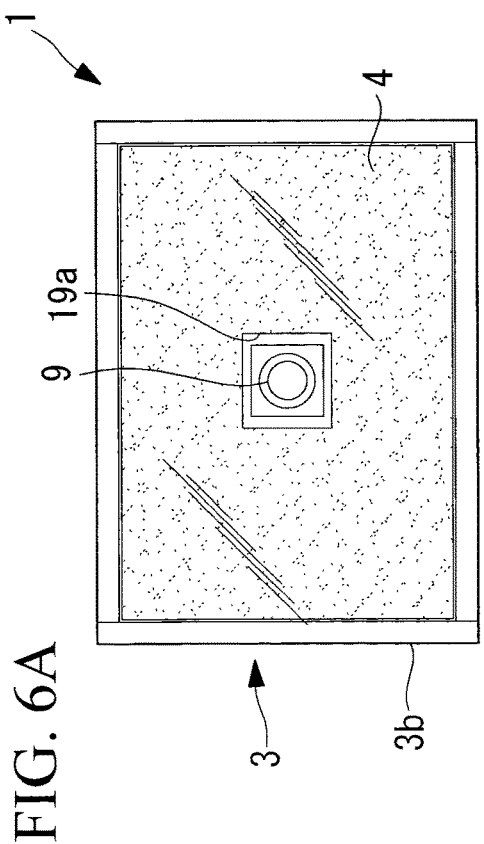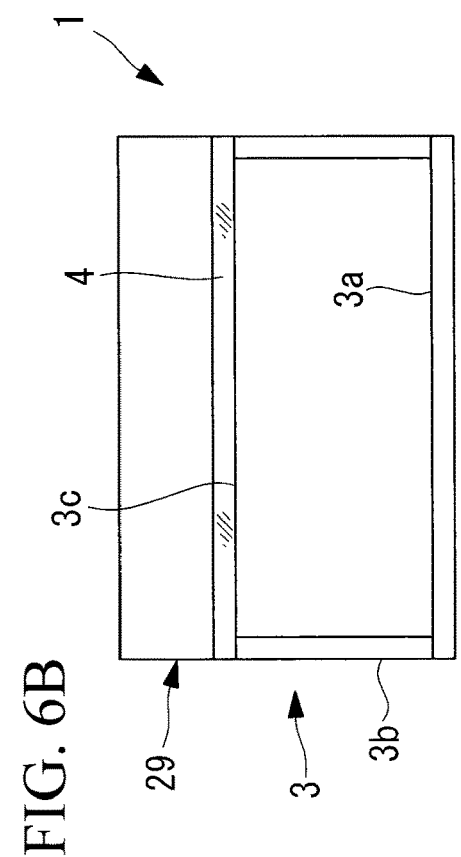

OBSERVATION APPARATUS

CROSS-REFERENCE TO RELATED APPLICATIONS

This application claims the benefit of Japanese Patent Application No. 2016-252699, the contents of which is incorporated herein by reference.

TECHNICAL FIELD

The present invention relates to an observation apparatus.

BACKGROUND ART

In the related art, there is a known observation apparatus with which cells that are being cultured in an incubator are observed (for example, see Patent Literature 1).

CITATION LIST

Patent Literature

{PTL 1} Japanese Unexamined Patent Application, Publication No. 2003-021628

SUMMARY OF INVENTION

An aspect of the present invention is an observation apparatus including: a housing that has, in a top face thereof, a transmission window on which a container accommodating a sample can be placed and through which light can pass; an image-acquisition portion that is accommodated in the housing and that captures observation light coming from the sample irradiated with illumination light and entering the housing by passing through the transmission window; and a housing-interior heating portion that is accommodated in the housing and that heats the sample.

BRIEF DESCRIPTION OF DRAWINGS

FIG. 6A is a top view showing an observation apparatus according to a fourth modification of the first embodiment of the present invention as viewed from above in a state in which the lid portion is removed therefrom.

FIG. 6B is a side view in which the observation apparatus in FIG. 6A is viewed from a side.

FIG. 6C is a sectional view in which the observation apparatus in FIG. 6B is cut through in the vertical direction.

FIG. 6D is a side view in which the observation apparatus in FIG. 6B is viewed from the side in a state in which the lid is open.

DESCRIPTION OF EMBODIMENTS

First Embodiment

An observation apparatus according to this embodiment will be described below with reference to the drawings.

Figure 1A:
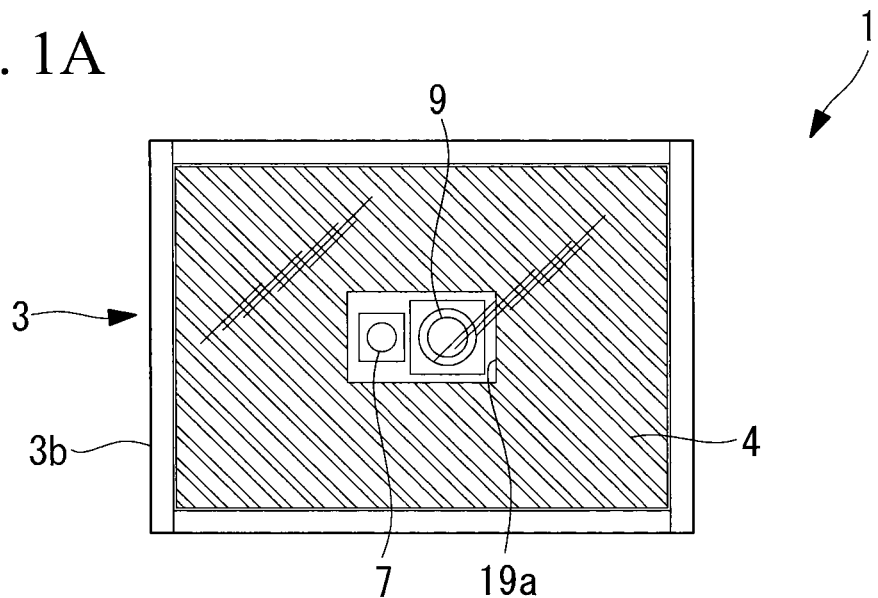
FIG. 1A is a top view showing an observation apparatus according to a first embodiment of the present invention as viewed from above.
Figure 1B:
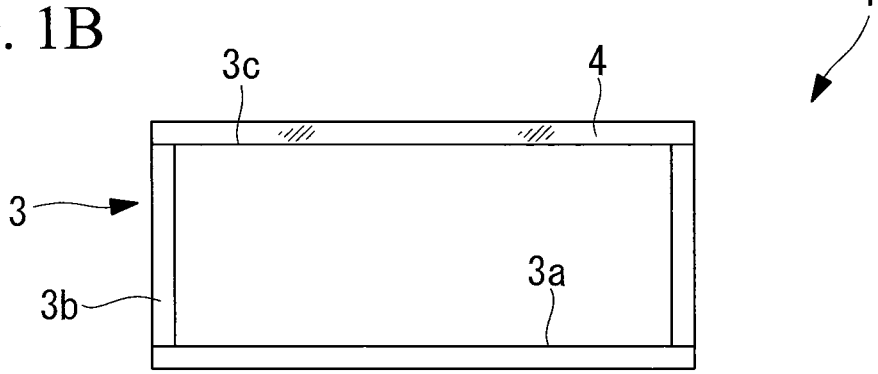
FIG. 1B is a side view in which the observation apparatus in FIG. 1A is viewed from a side.
Figure 1C:
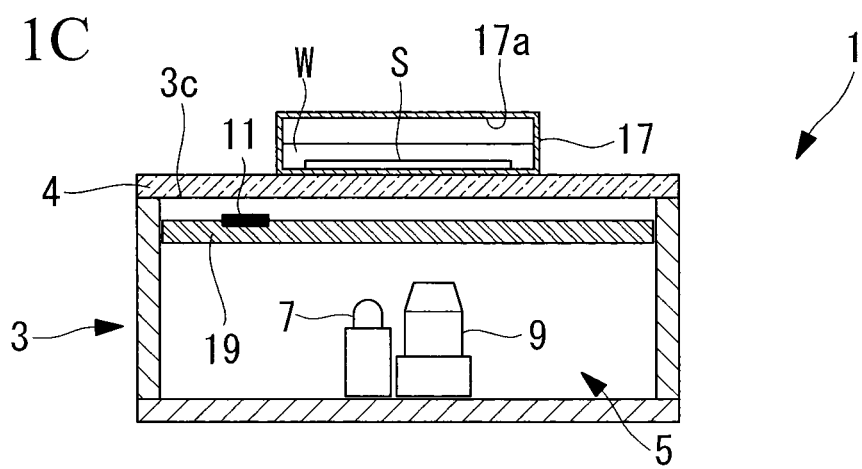
FIG. 1C is a sectional view in which the observation apparatus in FIG. 1B is cut through in the vertical direction.

As shown in FIGS. 1A, 1B, and 1C, an observation apparatus 1 of this embodiment is provided with: a housing 3; a housing-interior layer-like resistor (resistor) 19 that is accommodated in the housing 3 and that serves as a housing-interior heating portion 5; an illumination portion 7; a camera portion (image-acquisition portion) 9; and a temperature sensor 11.

Figure 2:
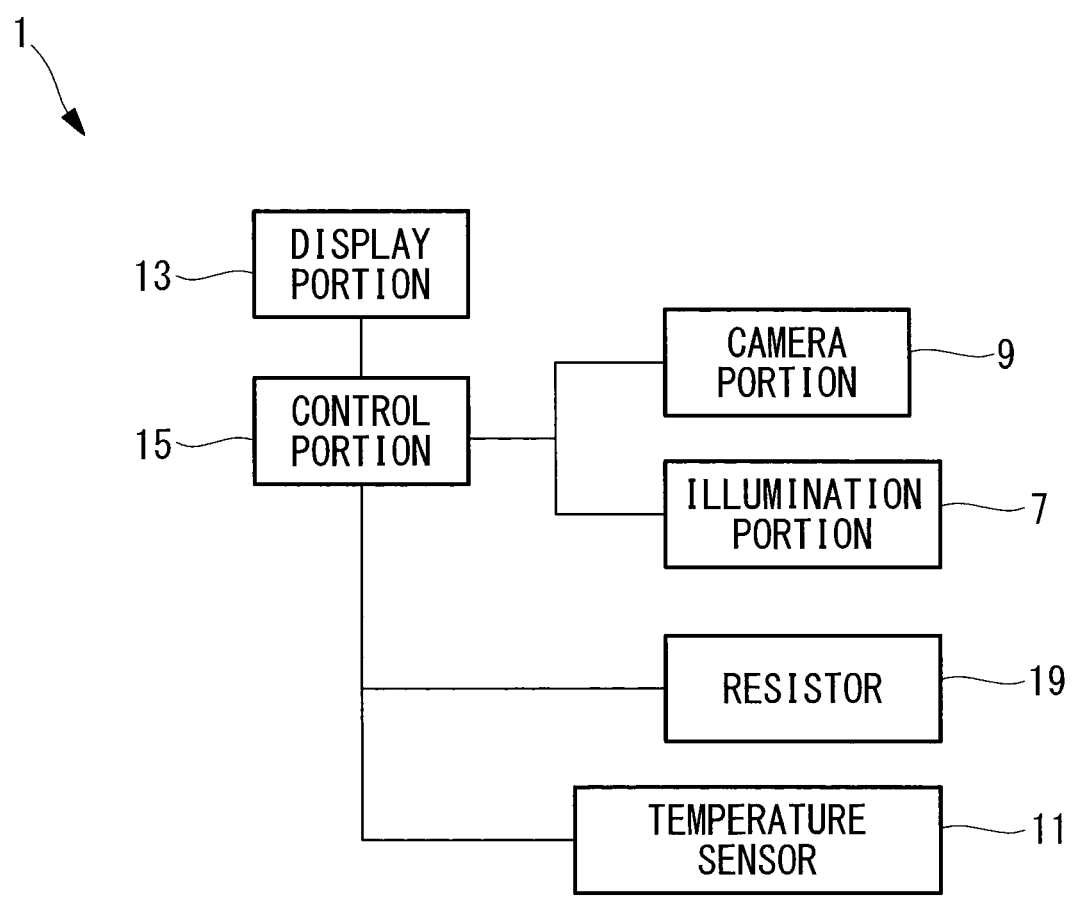
FIG. 2 is a block diagram showing the configuration of the observation apparatus according to the first embodiment of the present invention.

In addition, as shown in FIG. 2, the observation apparatus 1 is provided with: a display portion 13 that displays an image or the like acquired by the camera portion 9; and a control portion 15 that controls the illumination portion 7, the camera portion 9, the temperature sensor 11, the display portion 13, and the housing-interior layer-like resistor 19.

The housing 3 has, for example, a cuboid shape surrounded by: a bottom face 3a on which the illumination portion 7 and the camera portion 9 are placed; outer walls 3b that are erected on the bottom face 3a; and a top face 3c that is disposed so as to be parallel to the bottom face 3a with the outer walls 3b sandwiched therebetween.

The top face 3c of the housing 3 has a transmission window 4 on which a container 17 accommodating cells (sample) S can be placed.

The transmission window 4 is, for example, a hard, smooth glass plate that is disposed above the illumination portion 7 and the camera portion 9 so as to be substantially horizontal, and that is configured so as to allow light to pass therethrough. In addition, the transmission window 4 is configured so that it is possible to maintain a constant distance between the container 17 and the camera portion 9 in the optical-axis direction of the camera portion 9 and so that it is also possible to move the container 17 along a surface of the transmission window 4 and to maintain the container 17 at a certain position.

The container 17 is, for example, a cell-culturing flask having a top plate 17a, and is entirely formed of an optically transparent resin. The cells S are accommodated in the container 17 and are immersed in an aqueous solution such as a medium W or the like.

The housing-interior heating portion 5 is provided with the housing-interior layer-like resistor 19 that generates radiant heat by converting externally supplied electricity to heat.

The housing-interior layer-like resistor 19 is disposed in close proximity to the transmission window 4 of the housing 3 and parallel to the transmission window 4 with a gap between the transmission window 4 and the housing-interior layer-like resistor 19. This housing-interior layer-like resistor 19 is, for example, a carbon resistor or a metal-coated resistor, and is configured so as to heat the cells S in the container 17, which is placed on the transmission window 4, by generating radiant heat.

In addition, the housing-interior layer-like resistor 19 is formed in a rectangular shape, and gaps are formed between the outer walls 3b surrounding the peripheral area thereof and the housing-interior layer-like resistor 19. By doing so, it is possible to enhance the heat resistance of the housing-interior layer-like resistor 19. In addition, the housing-interior layer-like resistor 19 has an opening (through-hole) 19a that is provided on the optical axes of the illumination portion 7 and the camera portion 9.

The illumination portion 7 is disposed so that the position thereof is shifted in a direction that intersects the optical axis of the camera portion 9 and so as to face the transmission window 4 of the housing 3. The illumination portion 7 is configured so as to emit illumination light upward and to make the illumination light pass through the transmission window 4 and the bottom face of the container 17 upward from therebelow via the opening 19a of the housing-interior layer-like resistor 19 so that it is possible, subsequently, to radiate the illumination light onto the cells S from below or to cause the illumination light to be reflected at the top plate 17a of the container 17, thus radiating the illumination light onto the cells S from diagonally above.

The camera portion 9 is disposed facing the transmission window 4 of the housing 3. The camera portion 9 is configured so as that it is possible to capture, via the opening 19a of the housing-interior layer-like resistor 19, observation light coming from the cells S, examples of which include reflected light that passes through the bottom face of the container 17 and the transmission window 4 downward from thereabove when the illumination light coming from the illumination portion 7 is radiated onto the cells S from below and reflected at the cells S, and transmission light that passes through the bottom face of the container 17 and the transmission window 4 downward from thereabove when the illumination light coming from the illumination portion 7 is radiated onto the cells S from above via the top plate 17a of the container 17, thereby passing through the cells S, and so on.

The temperature sensor 11 is disposed on a surface of the housing-interior layer-like resistor 19 by facing the transmission window 4. The temperature sensor 11 measures the temperature of the housing-interior layer-like resistor 19, and transmits this information to the control portion 15 after converting the magnitude of the temperature to the magnitude of an electrical signal.

The display portion 13 displays, in addition to images acquired by the camera portion 9, for example, information about an instruction for capturing images by using the camera portion 9, a target temperature and the actual temperature of the cells S, a difference between the target temperature and the actual temperature, etc.

The control portion 15 is configured so as to control capturing of images of the cells S performed by the camera portion 9 and to save the images acquired by the camera portion 9, by executing a control program. In addition, the control portion 15 is configured so as to set the gain and the exposure time of the camera portion 9, and to set lighting conditions for the illumination portion 7.

Furthermore, the control portion 15 is configured so as, by executing the control program, to detect the difference between the target temperature and the temperature of the housing-interior layer-like resistor 19 measured by the temperature sensor 11; to supply power to the housing-interior layer-like resistor 19 if the actual temperature of the housing-interior layer-like resistor 19 is lower than the target temperature; and to stop supplying power to the housing-interior layer-like resistor 19 if the actual temperature of the housing-interior layer-like resistor 19 is greater than the target temperature.

The operation of the thus-configured observation apparatus 1 will now be described.

In order to observe the cells S by using the observation apparatus 1 according to this embodiment, first, radiant heat is generated by supplying power to the housing-interior layer-like resistor 19 by means of the control portion 15, and the temperature of the housing-interior layer-like resistor 19 is measured by means of the temperature sensor 11. Then, for example, the cells S that have been accommodated and cultured in the container 17 in an incubator (not shown) are placed, in the container 17, on the transmission window 4 of the housing 3.

Here, by placing the container 17 in close proximity to the housing-interior layer-like resistor 19 in the housing 3, it is possible to uniformly heat the cells S in the container 17 by means of the radiant heat emitted from the housing-interior layer-like resistor 19. In addition, because there is a high correlation between the temperatures of the housing-interior layer-like resistor 19 and the container 17 that are placed in close proximity to each other, it is possible to indirectly measure the temperature of the cells S in the container 17 on the basis of the temperature of the housing-interior layer-like resistor 19 itself measured by the temperature sensor 11.

Next, the control program is executed by the control portion 15, and the difference between the temperature of the housing-interior layer-like resistor 19 measured by the temperature sensor 11 and the target temperature is detected. Then, by means of the control portion 15, power is supplied to the housing-interior layer-like resistor 19 if the actual temperature of the housing-interior layer-like resistor 19 is lower than the target temperature, and the power supplied to the housing-interior layer-like resistor 19 is stopped if the actual temperature of the housing-interior layer-like resistor 19 is greater than the target temperature. By doing so, it is possible to maintain the state of the cells S in the container 17 at an appropriate temperature.

Next, in the state in which the cells S in the container 17 are heated by the housing-interior layer-like resistor 19, by means of the control portion 15, the camera portion 9 is driven and the illumination light is generated by the illumination portion 7. After being made to pass through the transmission window 4 of the housing 3 and the bottom face of the container 17 upward from therebelow via the opening 19a in the housing-interior layer-like resistor 19, the illumination light emitted from the illumination portion 7 is radiated onto the cells S from below and is radiated onto the cells S from diagonally above by being reflected by the top plate 17a of the container 17.

The observation light coming from the cells S, examples of which include reflected light that is reflected at the cells S when the illumination light is radiated thereonto from below, transmission light that passes through the cells S when the illumination light is radiated thereonto from above, and so on, pass through the bottom face of the container 17 and the transmission window 4 of the housing 3 downward from thereabove, and are received by the camera portion 9 after passing through the opening 19a in the housing-interior layer-like resistor 19.

At this time, the illumination light is refracted and scattered depending on the shapes of the cells S and the refractive index thereof, or the illumination light is dimmed depending on the reflectance or the transmittance of the cells S, thereby being converted to observation light carrying information about the cells S and captured by the camera portion 9. The images of the cells S acquired by the camera portion 9 are transmitted to and displayed on the display portion 13.

As has been described above, with the observation apparatus 1 according to this embodiment, by acquiring images of the cells S by capturing images thereof while heating the cells S in the container 17 by means of the housing-interior layer-like resistor 19 in the housing 3, it is possible to observe the cells S that have been cultured at an appropriate temperature by using an incubator, while maintaining the state thereof at the appropriate temperature.

In this embodiment, because there is a high correlation between the temperature of the housing-interior layer-like resistor 19 and the temperature of the container 17, it is possible to indirectly ascertain changes in the temperature of the cells S on the basis of the resistance of the housing-interior layer-like resistor 19 itself. Therefore, for example, the temperature of the housing-interior layer-like resistor 19 may be adjusted on the basis of the resistance of the housing-interior layer-like resistor 19 itself without providing the temperature sensor 11, or the temperature of the housing-interior layer-like resistor 19 may be adjusted by using the temperature measurement by means of the temperature sensor 11 in combination with the resistance of the housing-interior layer-like resistor 19 itself.

This embodiment can be modified as below.

Figure 3A:
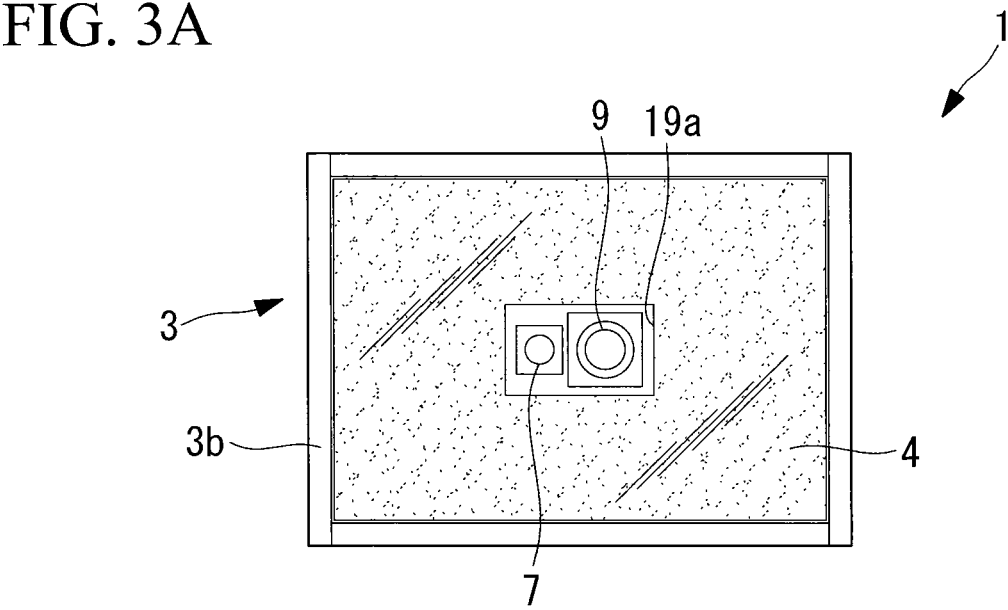
FIG. 3A is a top view showing an observation apparatus according to a first modification of the first embodiment of the present invention as viewed from above.
Figure 3B:
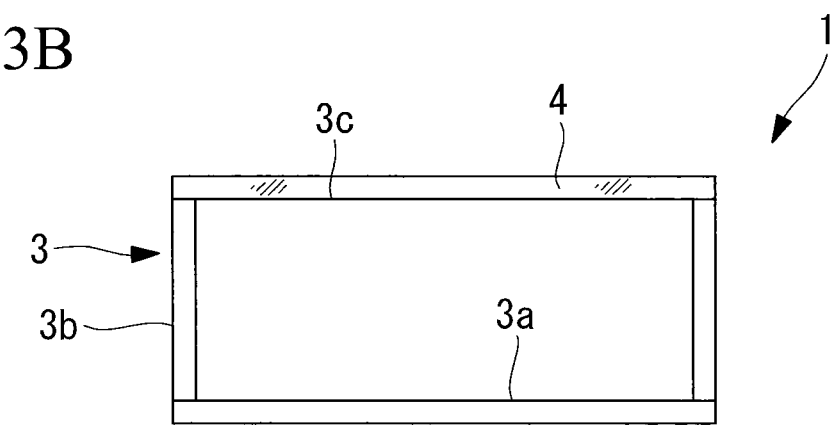
FIG. 3B is a side view in which the observation apparatus in FIG. 3A is viewed from a side.
Figure 3C:
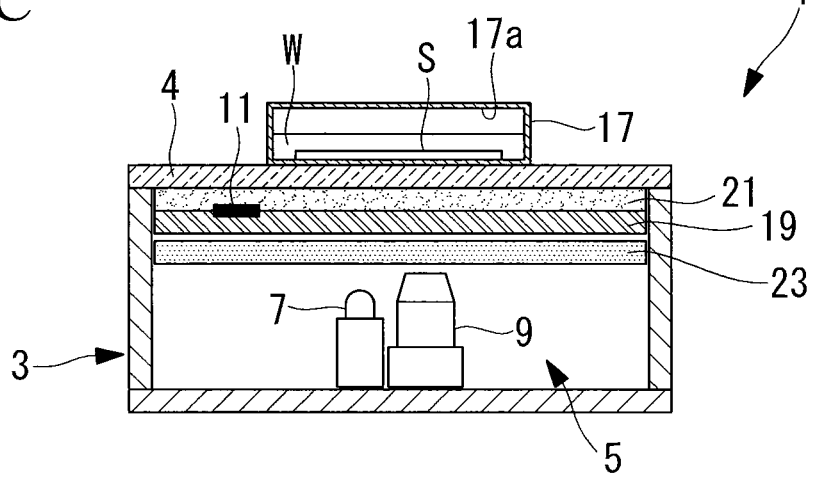
FIG. 3C is a sectional view in which the observation apparatus in FIG. 3B is cut through in the vertical direction.

As a first modification, for example, as shown in FIGS. 3A, 3B, and 3C, the housing-interior heating portion 5 may be provided with a housing-interior radiation layer 21 that makes the radiation of radiant heat emitted from the housing-interior layer-like resistor 19 uniform.

As the housing-interior radiation layer 21, for example, an aluminum plate painted in matte black, having a high heat emissivity and conductivity, may be employed. In addition, the housing-interior radiation layer 21 may be disposed between the transmission window 4 of the housing 3 and the housing-interior layer-like resistor 19. In addition, as with the housing-interior layer-like resistor 19, the housing-interior radiation layer 21 may have an opening that is provided on the optical axes of the illumination portion 7 and the camera portion 9. The housing-interior radiation layer 21 and the transmission window 4 may be in contact with each other or may have a gap therebetween, and the housing-interior radiation layer 21 and the housing-interior layer-like resistor 19 may be in contact with each other or may have a gap therebetween.

With this modification, it is possible to more uniformly heat the cells S by causing the radiant heat from the housing-interior layer-like resistor 19 to be uniformly conducted to the cells S in the container 17 by means of the housing-interior radiation layer 21. Note that it is desirable that the housing-interior radiation layer 21 have gaps between the outer walls 3b that surround the peripheral area thereof and the housing-interior radiation layer 21. By doing so, it is possible to enhance the heat resistance of the housing-interior radiation layer 21.

In addition, in this modification, as shown in the aforementioned drawings, the housing-interior heating portion 5 may be provided with a housing-interior reflection layer 23 that reflects the radiant heat emitted from the housing-interior layer-like resistor 19.

As the housing-interior reflection layer 23, for example, a mirror-finished aluminum plate having a high reflectance with respect to infrared light may be employed. In addition, the housing-interior reflection layer 23 may be disposed on the opposite side from the transmission window 4 of the housing 3 with the housing-interior layer-like resistor 19 sandwiched therebetween. In addition, as with the housing-interior layer-like resistor 19, the housing-interior reflection layer 23 may also have an opening that is provided on the optical axes of the illumination portion 7 and the camera portion 9.

By doing so, the radiant heat emitted from the housing-interior layer-like resistor 19 in the direction opposite side from the cells S is reflected by the housing-interior reflection layer 23 and is conducted to the cells S, and thus, it is possible to more efficiently heat the cells S. Note that it is desirable that the housing-interior reflection layer 23 and the housing-interior layer-like resistor 19 have a gap therebetween, and that the housing-interior reflection layer 23 and the outer walls 3b surrounding the peripheral area thereof have gaps therebetween. By doing so, it is possible to enhance the heat resistance of the housing-interior reflection layer 23.

Figure 4A:
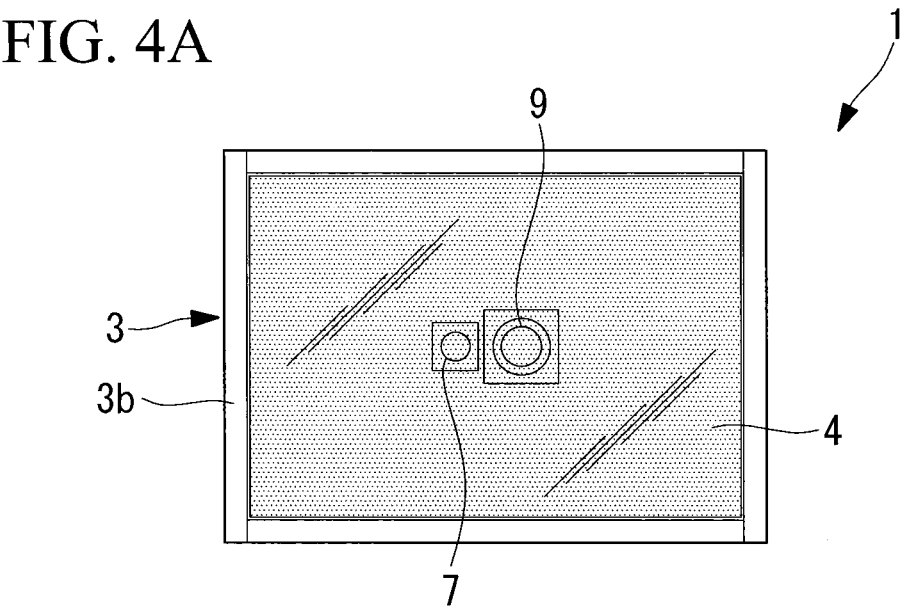
FIG. 4A is a top view showing an observation apparatus according to a second modification of the first embodiment of the present invention as viewed from above.
Figure 4B:
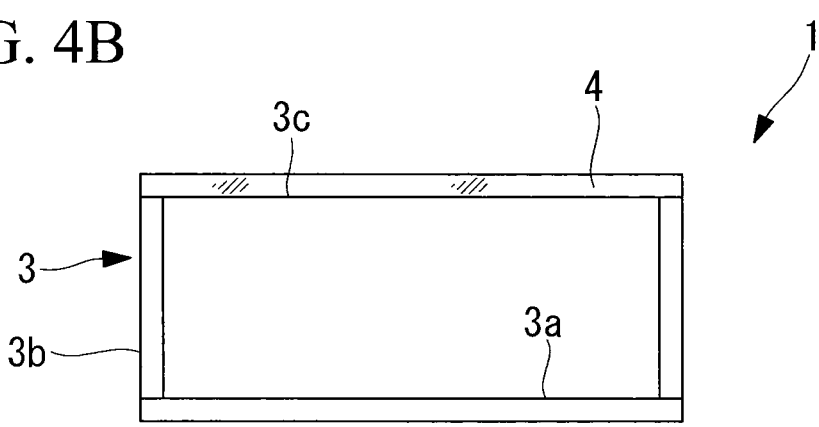
FIG. 4B is a side view in which the observation apparatus in FIG. 4A is viewed from a side.
Figure 4C:
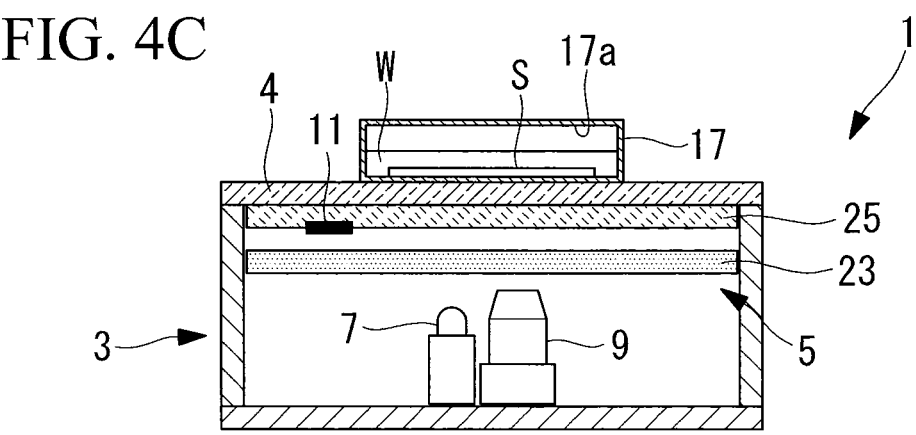
FIG. 4C is a sectional view in which the observation apparatus in FIG. 4B is cut through in the vertical direction.

As a second modification, for example, as shown in FIGS. 4A, 4B, and 4C, the housing-interior heating portion 5 may employ a transparent metal film 25, such as an ITO (Indium Tin Oxide) film or the like, instead of the housing-interior layer-like resistor 19.

The transparent metal film 25 is disposed, for example, on an inner surface of the transmission window 4, and is configured so as to generate heat by converting externally supplied electricity, thus making it possible to heat the cells S in the container 17 placed on the transmission window 4. In addition, the transparent metal film 25 is configured so as to allow the illumination light coming from the illumination portion 7 to pass therethrough and to allow the observation light, examples of which include reflected light, transmission light, and so forth coming from the cells S, to pass therethrough. Note that it is preferable that the transparent metal film 25 have gaps between the outer walls 3b surrounding the peripheral area thereof and the transparent metal film 25. By doing so, it is possible to enhance the heat resistance of the transparent metal film 25.

In this case, the temperature sensor 11 may be disposed on a surface of the transparent metal film 25 facing the illumination portion 7 and the camera portion 9 to measure the temperature of the transparent metal film 25, and may convert the magnitude of the temperature to the magnitude of an electrical signal to be transmitted to the control portion 15. Because there is a high correlation between the temperature of the transparent metal film 25 and the temperature of the container 17 since the transparent metal film 25 is disposed in close proximity to the container 17 on the transmission window 4, by measuring the temperature of the transparent metal film 25 by means of the temperature sensor 11, it is possible to indirectly ascertain changes in the temperature of the cells S in the container 17.

In addition, the control portion 15 may, by executing the control program: detect the difference between the target temperature and the temperature of the transparent metal film 25 measured by the temperature sensor 11; supply power to the transparent metal film 25 if the actual temperature of the transparent metal film 25 is lower than the target temperature; and stop supplying power to the transparent metal film 25 if the actual temperature of the transparent metal film 25 is greater than the target temperature.

In this modification, because there is a high correlation between the temperature of the transparent metal film 25 and the temperature of the container 17, it is possible to indirectly ascertain changes in the temperature of the cells S on the basis of the resistance of the transparent metal film 25 itself. Therefore, for example, the temperature of the transparent metal film 25 may be adjusted on the basis of the resistance of the transparent metal film 25 itself without providing the temperature sensor 11 or the temperature of the transparent metal film 25 may be adjusted by using the temperature measurement by means of the temperature sensor 11 in combination with the resistance of the transparent metal film 25.

With this modification, it is possible to capture, by means of the camera portion 9, the observation light that is coming from the cells S and that has passed through the transmission window 4 of the housing 3 by making the observation light pass through the transparent metal film 25. Therefore, it is not necessary to provide an opening (through-hole) in the transparent metal film 25 to allow the observation light to pass therethrough.

In this modification, as with the first modification, the housing-interior heating portion 5 may be provided with the housing-interior reflection layer 23.

As a third modification, for example, as shown in FIGS. 5A, 5B, 5C, and 5D, it is permissible to provide an opening/closing-type lid portion 29 with which a sealed space 27 can be formed in the peripheral area of the container 17 placed on the transmission window 4 of the housing 3.

By forming the sealed space 27 in the peripheral area of the container 17 by using the lid portion 29, it is possible to suppress escape of the heat of the cells S to the exterior.

In this modification, as with the first modification, the housing-interior heating portion 5 may be provided with the housing-interior radiation layer 21 and the housing-interior reflection layer 23.

Figure 5A:
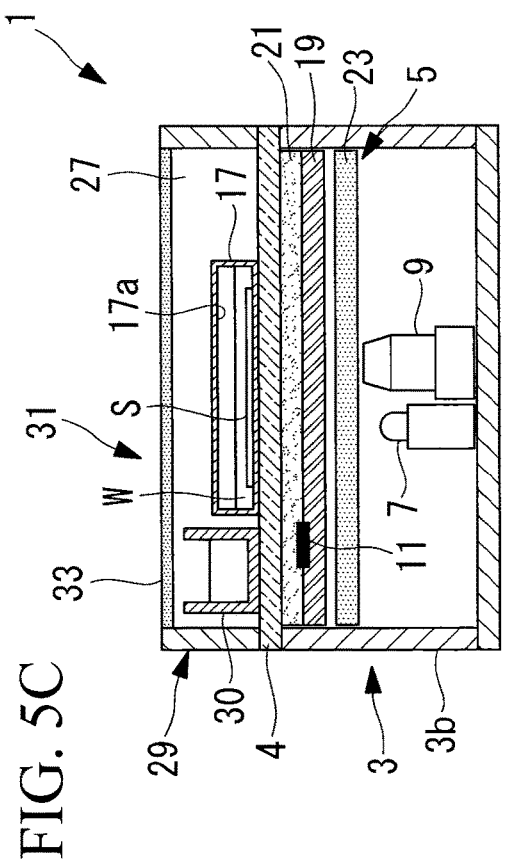
FIG. 5A is a top view showing an observation apparatus according to a third modification of the first embodiment of the present invention as viewed from above in a state in which a lid portion is removed therefrom.
Figure 5C:
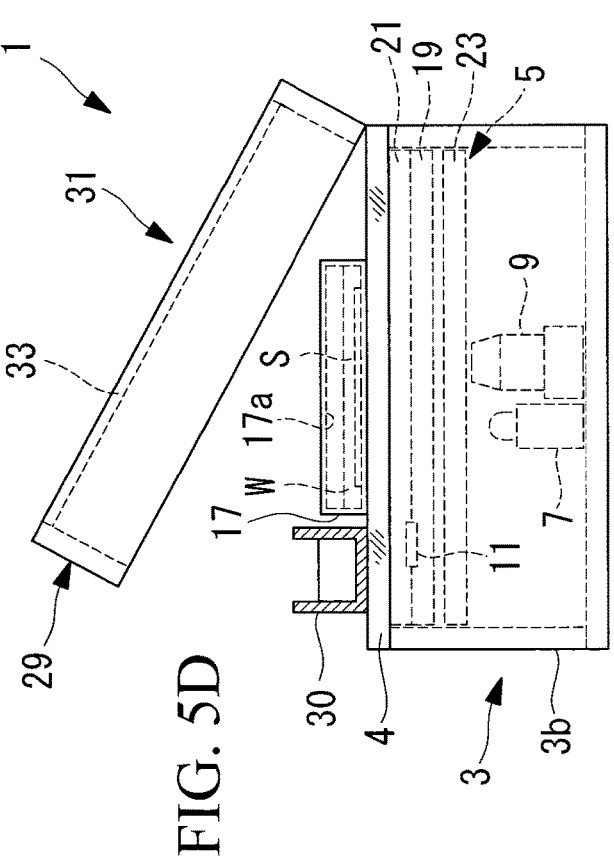
FIG. 5C is a sectional view in which the observation apparatus in FIG. 5B is cut through in the vertical direction.
Figure 5B:
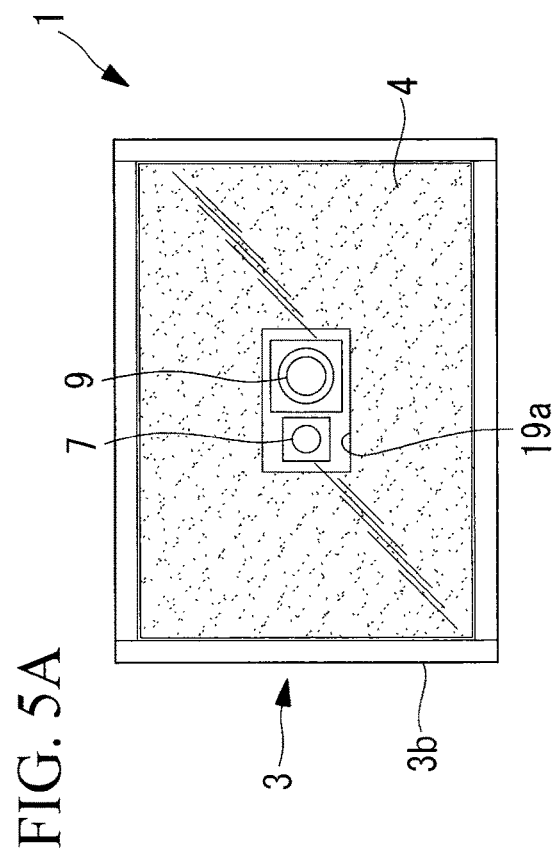
FIG. 5B is a side view in which the observation apparatus in FIG. 5A is viewed from a side.
Figure 5D:
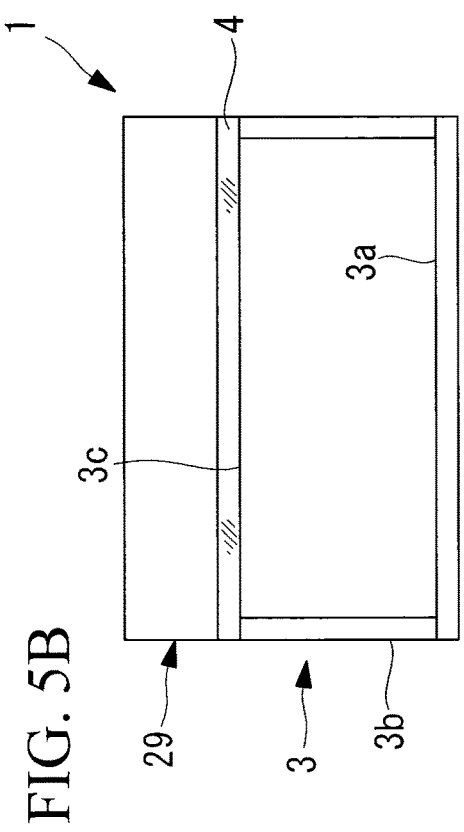
FIG. 5D is a side view in which the observation apparatus in FIG. 5B is viewed from the side in a state in which a lid is open.
Figure 7A:
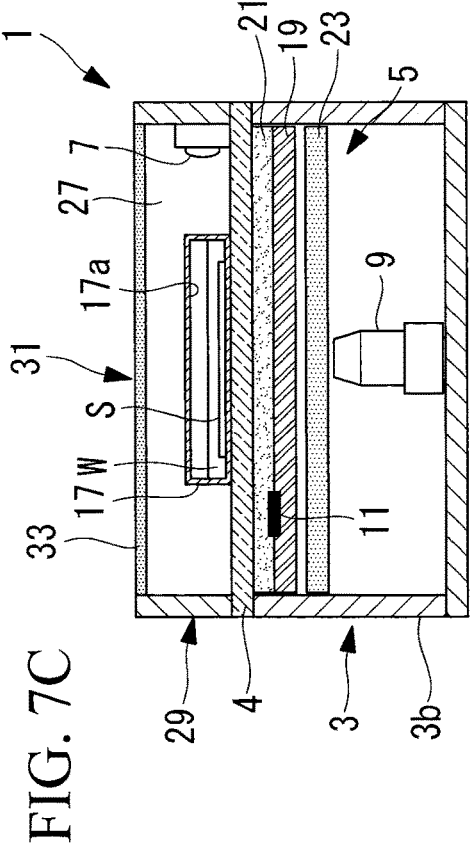
FIG. 7A is a top view showing an observation apparatus according to a fifth modification of the first embodiment of the present invention as viewed from above in a state in which the lid portion is removed therefrom.
Figure 7C:
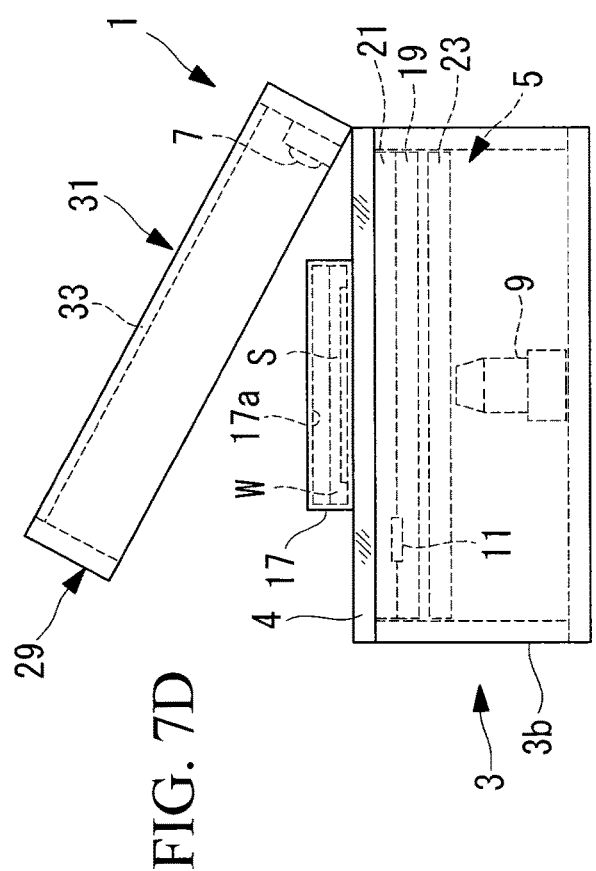
FIG. 7C is a sectional view in which the observation apparatus in FIG. 7B is cut through in the vertical direction.
Figure 7B:
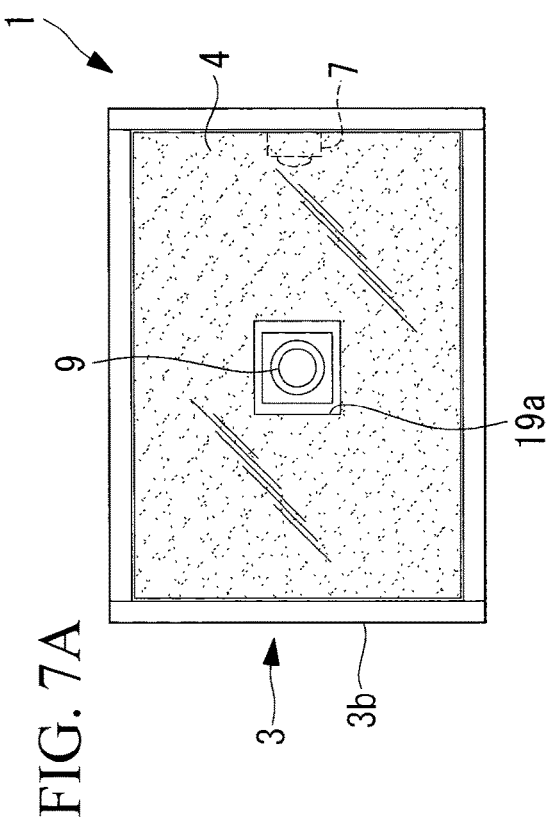
FIG. 7B is a side view in which the observation apparatus in FIG. 7A is viewed from a side.
Figure 7D:
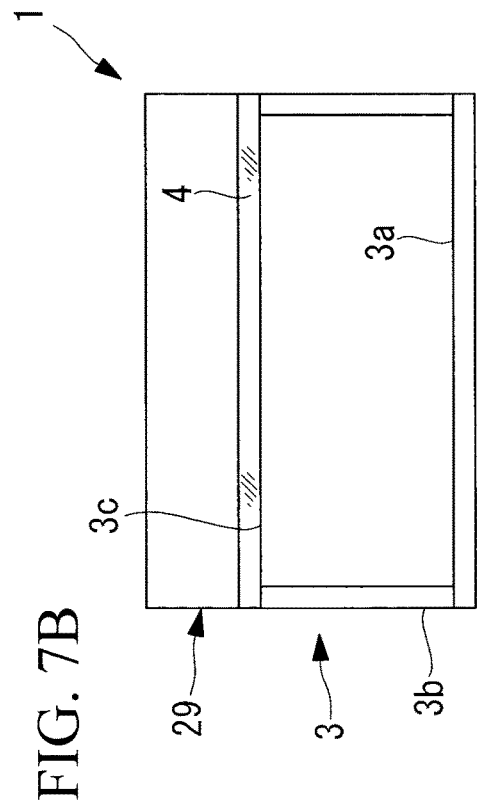
FIG. 7D is a side view in which the observation apparatus in FIG. 7B is viewed from the side in a state in which the lid is open.
Figure 8A:
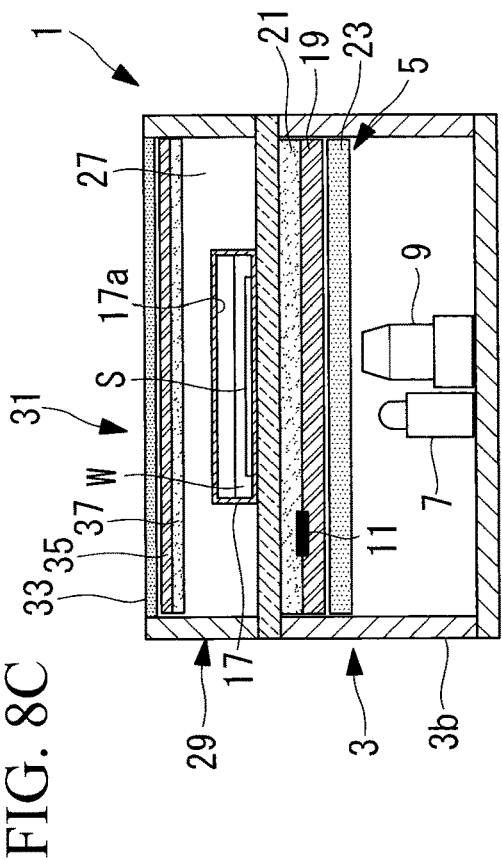
FIG. 8A is a top view showing an observation apparatus according to a sixth modification of the first embodiment of the present invention as viewed from above in a state in which the lid portion is removed therefrom.
Figure 8C:
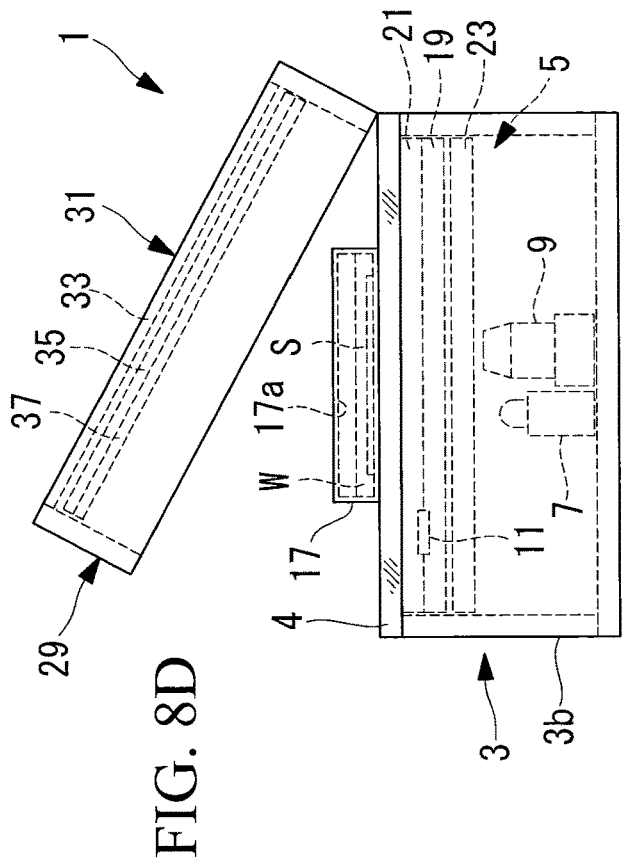
FIG. 8C is a sectional view in which the observation apparatus in FIG. 8B is cut through in the vertical direction.
Figure 8B:
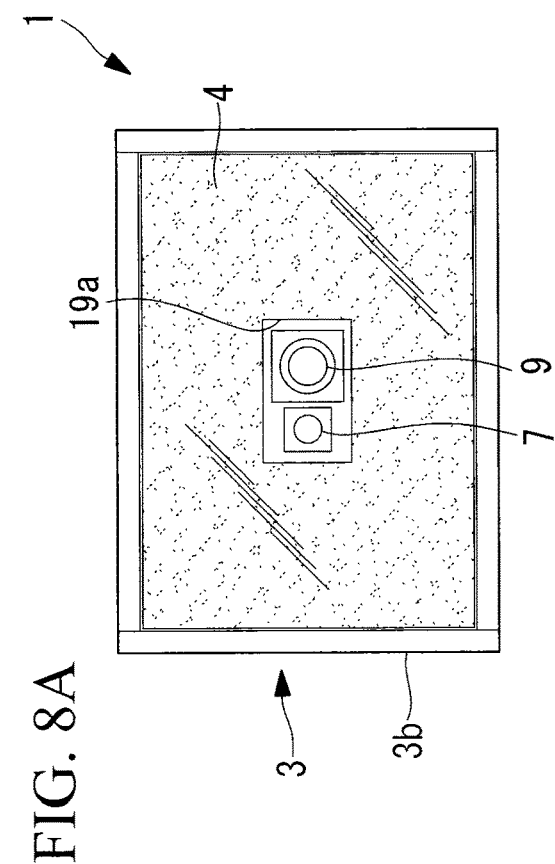
FIG. 8B is a side view in which the observation apparatus in FIG. 8A is viewed from a side.
Figure 8D:
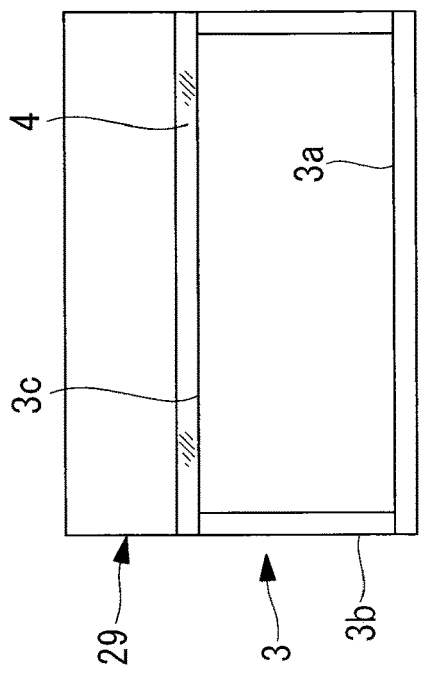
FIG. 8D is a side view in which the observation apparatus in FIG. 8B is viewed from the side in a state in which the lid is open.

In addition, in this modification, as shown in FIGS. 5C and 5D, a lid-interior heating portion 31 that is disposed in the sealed space 27 formed by the lid portion 29 and that heats the cells S in the container 17 may be provided in addition to the housing-interior heating portion 5 provided in the housing 3.

The lid-interior heating portion 31 may be provided with a lid-interior reflection layer 33 that reflects, toward the container 17, the radiant heat conducted from the housing-interior layer-like resistor 19 to the sealed space 27 and the illumination light coming from the illumination portion 7. In this case, a top plate of the lid portion 29 facing the transmission window 4 of the housing 3 may be configured by using the lid-interior reflection layer 33. As the lid-interior reflection layer 33, a reflection layer having a similar configuration to that of the housing-interior reflection layer 23 may be employed.

By doing so, by reflecting the radiant heat conducted to the sealed space 27 from the housing-interior layer-like resistor 19 by means of the lid-interior reflection layer 33, it is possible to guide the radiant heat to the cells S in the container 17. By heating the container 17 also from above by means of the lid-interior reflection layer 33, it is possible to reduce the nonuniformities in the temperature of the cells S and fogging of the container 17. Note that the lid-interior reflection layer 33 may be disposed between the top plate of the lid portion 29 and the container 17 instead of forming the top plate of the lid portion 29.

In this modification, as shown in FIGS. 5C and 5D, a container (humidifying pad) 30 having $H_2O$ (liquid water) inside thereof may be placed in the sealed space 27. By doing so, by filling the sealed space 27 with saturated vapor by causing $H_2O$ in the container 30 to be evaporated, it is possible to reduce the amount by which the medium W in the container 17 is evaporated. The container 30 may also be provided in a similar manner in fourth, fifth, and sixth modifications of this embodiment and first, second, and third modifications of a third embodiment, described later.

As the fourth modification, as shown in FIGS. 6A, 6B, 6C, and 6D, in the configuration of the third modification, the illumination portion 7, instead of being disposed on the bottom face 3a of the housing 3, may be disposed on the optical axis of the camera portion 9 in the lid-interior reflection layer 33 of the lid portion 29 so as to face the housing 3. In this case, when light is emitted from the illumination portion 7, it is permissible to capture, by using the camera portion 9, transmission light that has passed through the cells S in the container 17, and that has additionally passed through the bottom face of the container 17 and the transmission window 4 of the housing 3.

As the fifth modification, as shown in FIGS. 7A, 7B, 7C, and 7D, instead of the configuration of the fourth modification, the illumination portion 7 may be disposed on the inner surface of the lid portion 29 instead of the lid-interior reflection layer 33 of the lid portion 29. In this case, when light is emitted from the illumination portion 7, it is permissible to capture, by means of the camera portion 9, the transmission light that has passed through the cells S in the container 17, and that has additionally passed through the bottom face of the container 17 and the transmission window 4, or the reflected light that has been reflected at the cells S, and that has additionally passed through the bottom face of the container 17 and the transmission window 4.

As the sixth modification, as shown in FIGS. 8A, 8B, 8C, and 8D, in the configuration of the third modification, the lid-interior heating portion 31 may be provided with a lid-interior layer-like resistor 35 that generates radiant heat.

The lid-interior layer-like resistor 35 may have a similar configuration to that of the housing-interior layer-like resistor 19 and may be disposed parallel to the transmission window 4 in close proximity to the container 17 above the container 17 (between the container 17 and the lid-interior reflection layer 33) and so as to have a gap between the container 17 and the lid-interior layer-like resistor 35. It is preferable that the lid-interior layer-like resistor 35 have gaps between side surfaces of the lid portion 29 surrounding the peripheral area thereof and the lid-interior layer-like resistor 35. By doing so, it is possible to enhance the heat resistance of the lid-interior layer-like resistor 35.

With this modification, it is possible to efficiently heat the cells S over the entire container 17 by using the lid-interior layer-like resistor 35 disposed so as to face the bottom face of the container 17 in combination with heating by means of the housing-interior heating portion 5. In addition, the radiant heat emitted from the lid-interior layer-like resistor 35 in the direction opposite side from the container 17 is also conducted to the cells S by means of the lid-interior reflection layer 33 disposed above the container 17, and thus, it is possible to more efficiently heat the cells S.

In this modification, as shown in the aforementioned drawings, the lid-interior heating portion 31 may be provided with a lid-interior radiation layer 37 that makes the radiation of the radiant heat emitted from the lid-interior layer-like resistor 35 uniform. The lid-interior radiation layer 37 may have a similar configuration to that of the housing-interior radiation layer 21 and may be disposed between the container 17 and the lid-interior layer-like resistor 35.

By doing so, it is possible to more uniformly heat the cells S by causing the radiant heat from the lid-interior layer-like resistor 35 to be uniformly conducted thereto by means of the lid-interior radiation layer 37.

Second Embodiment

Next, an observation apparatus according to a second embodiment of the present invention will be described below with reference to the drawings.

As shown in FIGS. 9A, 9B, 9C, and 10, an observation apparatus 41 according to this embodiment differs from that of the first embodiment in that the observation apparatus 41 is provided with the opening/closing-type lid portion 29 with which the sealed space 27 can be formed in the peripheral area of the container 17 placed on the transmission window 4 of the housing 3, and, additionally, structures for externally supplying $CO_2$ and $H_2O$ (vapor) to the sealed space 27 formed by the lid portion 29.

In describing this embodiment, portions having configurations that are the same as those in the observation apparatus 1 according to the first embodiment, described above, will be given the same reference signs, and descriptions thereof will be omitted.

Figure 9A:
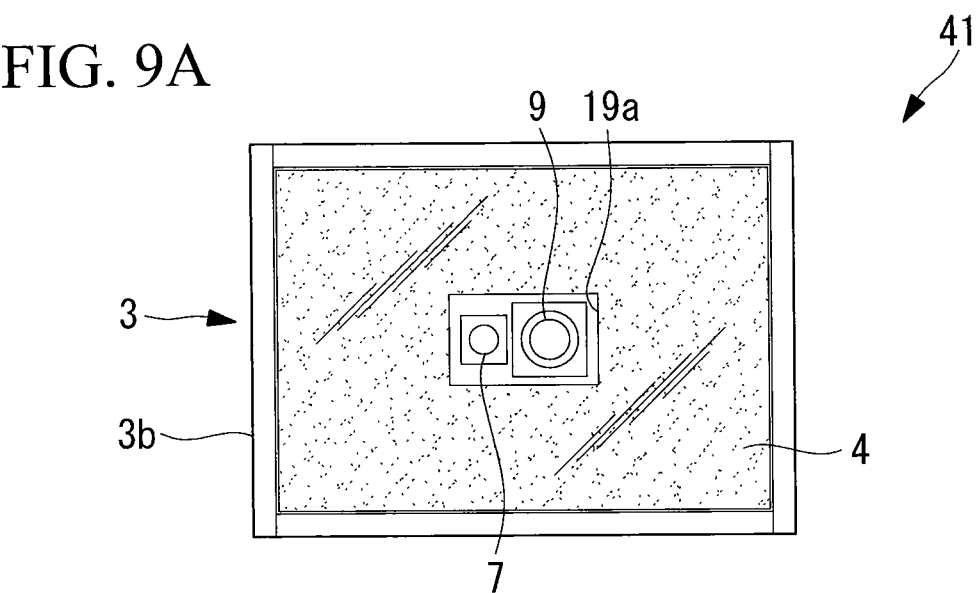
FIG. 9A is a top view showing an observation apparatus according to a second embodiment of the present invention as viewed from above.
Figure 9B:
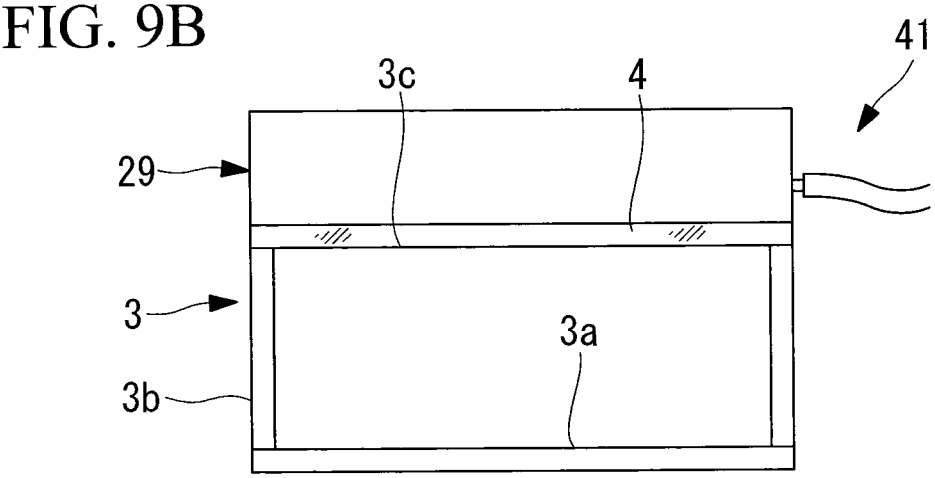
FIG. 9B is a side view in which the observation apparatus in FIG. 9A is viewed from a side.
Figure 9C:
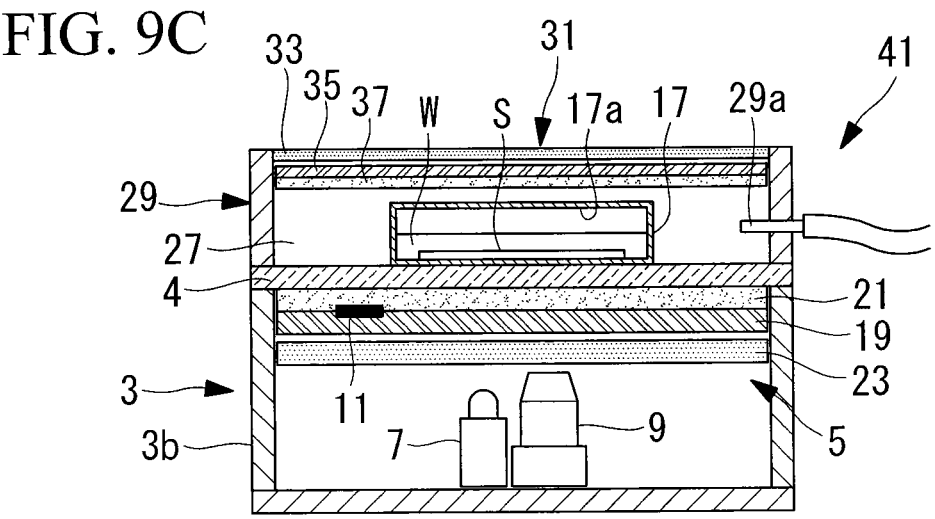
FIG. 9C is a sectional view in which the observation apparatus in FIG. 9B is cut through in the vertical direction.
Figure 10:
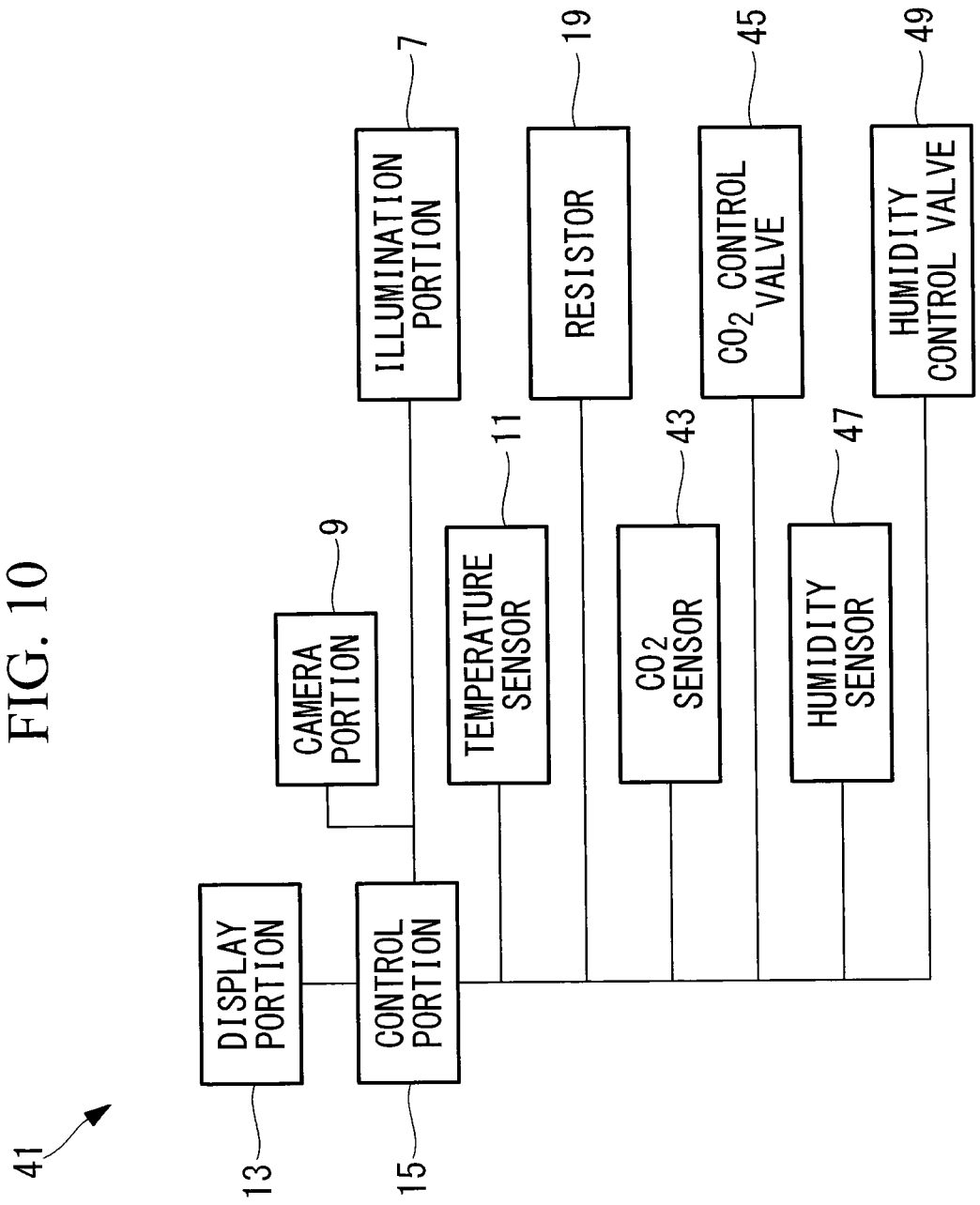
FIG. 10 is a block diagram showing the configuration of the observation apparatus according to the second embodiment of the present invention.
Figure 11A:
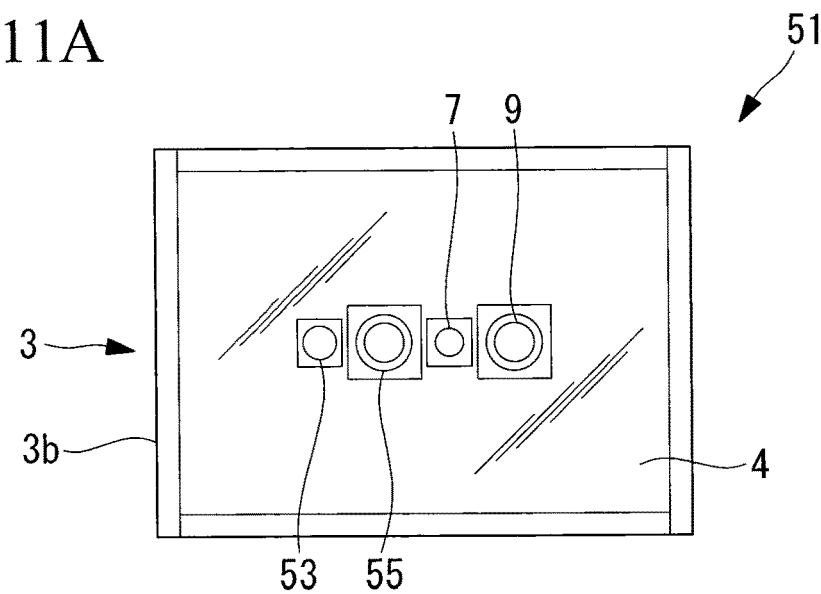
FIG. 11A is a top view showing an observation apparatus according to a third embodiment of the present invention as viewed from above.
Figure 11B:
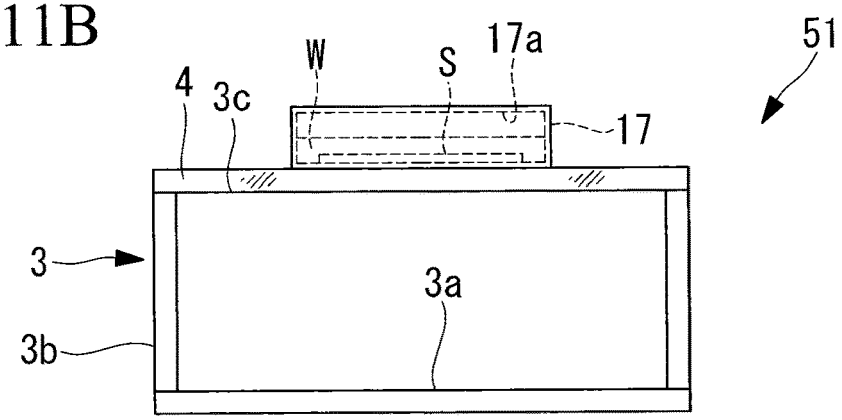
FIG. 11B is a side view in which the observation apparatus in FIG. 11A is viewed from a side.
Figure 11C:
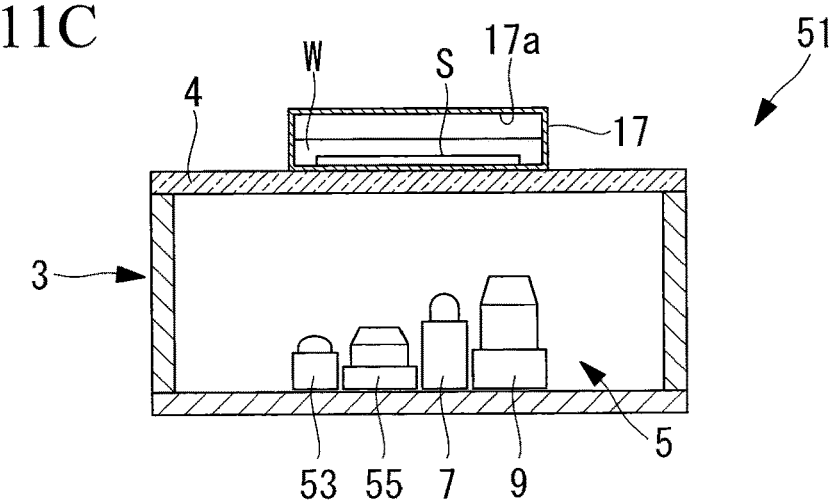
FIG. 11C is a sectional view in which the observation apparatus in FIG. 11B is cut through in the vertical direction.
Figure 12:
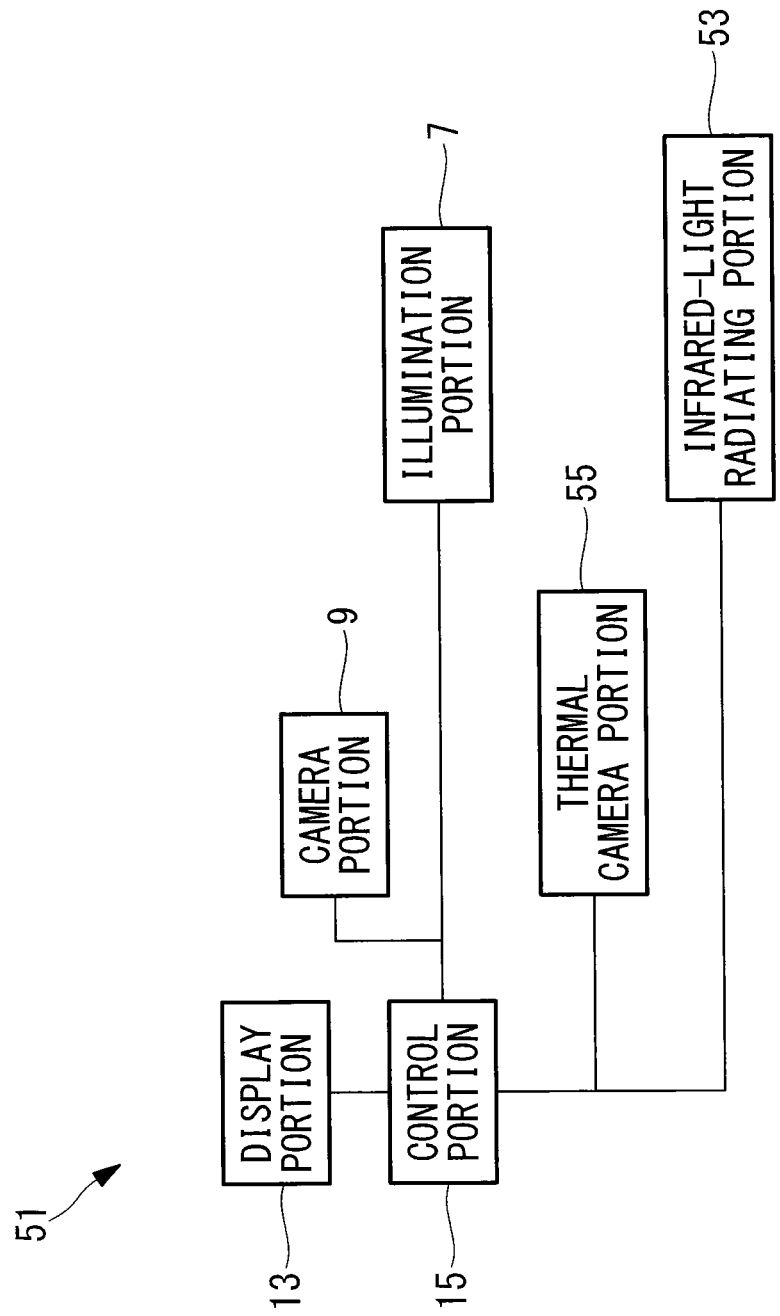
FIG. 12 is a block diagram showing the configuration of the observation apparatus according to the third embodiment of the present invention.

As shown in FIG. 9C, the observation apparatus 41 includes a gas supply port 29a in the lid portion 29 as a structure for supplying $CO_2$ and $H_2O$ to the sealed space 27. In addition, as shown in FIG. 10, the observation apparatus 41 is provided with, as the structures for supplying $CO_2$ and $H_2O$ to the sealed space 27: a $CO_2$ storage portion (not shown) that stores $CO_2$, such as a $CO_2$ canister or the like; a $CO_2$ sensor 43 that measures the $CO_2$ concentration in the sealed space 27; a $CO_2$ control valve 45 with which it is possible to change the amount of supplied $CO_2$; an $H_2O$ generating portion (not shown) that generates $H_2O$ (vapor); a humidity sensor 47 that measures the humidity in the sealed space 27; and a humidity control valve 49 with which it is possible to change the amount of supplied $H_2O$.

The $CO_2$ sensor 43 is configured so as to transmit the measured $CO_2$ concentration in the sealed space 27 to the control portion 15.

The humidity sensor 47 is configured so as to transmit the measured humidity in the sealed space 27 to the control portion 15.

The control portion 15 compares the $CO_2$ concentration transmitted thereto from the $CO_2$ sensor 43 to a target $CO_2$ value, and adjusts the amount of supplied $CO_2$ by means of the $CO_2$ control valve 45 so that the $CO_2$ concentration in the sealed space 27 reaches the target $CO_2$ value. In addition, the control portion 15 compares the humidity transmitted thereto from the humidity sensor 47 to a target humidity, and adjusts the amount of supplied $H_2O$ by means of the humidity control valve 49 so that the humidity in the sealed space 27 reaches the target humidity.

With the thus-configured observation apparatus 41, by managing the $CO_2$ concentration and the humidity in the sealed space 27 by means of the structures for supplying $CO_2$ and $H_2O$ to the sealed space 27, it is possible to observe the cells S while culturing the cells S in an appropriate environment.

Third Embodiment

Next, an observation apparatus according to the third embodiment of the present invention will be described below with reference to the drawings.

As shown in FIGS. 11A, 11B, 11C, and 12, an observation apparatus 51 according to this embodiment differs from those of the first and second embodiments in that the housing-interior heating portion 5 is provided with: an infrared-light radiating portion (housing-interior infrared-light generating portion) 53 that radiates infrared light onto a medium in the container 17 instead of the housing-interior layer-like resistor 19; and, as a temperature sensor, a thermal camera portion (thermal camera) 55 that measures the temperature of the medium accommodated in the container 17 instead of the temperature sensor 11.

In describing this embodiment, portions having configurations that are the same as those in the observation apparatus 1 according to the first embodiment and the observation apparatus 41 according to the second embodiment, described above, will be given the same reference signs, and descriptions thereof will be omitted.

The infrared-light radiating portion 53 is disposed on the bottom face 3a of the housing 3 so that the position thereof is shifted in a direction that intersects the optical axis of the camera portion 9. The infrared-light radiating portion 53 emits infrared light upward, and radiates the infrared light onto the medium W in the container 17 from below after making the infrared light pass through the transmission window 4 of the housing 3 and the bottom face of the container 17 upward from therebelow.

In addition, the infrared-light radiating portion 53 is configured so as to generate infrared light at 1450 nm±50 nm or 1940 nm±50 nm. Because 1450 nm and 1940 nm are the absorption wavelengths of water, it is possible to efficiently heat, via an aqueous solution such as the medium W or the like, the cells S by means of the infrared light emitted from the infrared-light radiating portion 53.

The thermal camera portion 55 is disposed on the bottom face 3a of the housing 3 so that the position thereof is shifted in a direction that intersects the optical axis of the camera portion 9, for example, next to the infrared-light radiating portion 53. The thermal camera portion 55 measures the temperature of the medium W on the basis of the heat energy generated in the medium W in the container 17 irradiated with the infrared light coming from the infrared-light radiating portion 53, and transmits this information to the control portion 15 after converting the magnitude of the temperature to the magnitude of a pixel value.

The control portion 15 is configured so as, by executing the control program: to detect the difference between the target temperature and the temperature of the medium W measured by the thermal camera portion 55; to cause the infrared-light radiating portion 53 to emit the infrared light if the actual temperature of the medium W is lower than the target temperature; and to cause the infrared-light radiating portion 53 to stop emitting the infrared light if the actual temperature of the medium W is greater than the target temperature. In addition, the control portion 15 is configured so as to cause the infrared-light radiating portion 53 to stop emitting the infrared light when the thermal camera portion 55 is capturing an image.

The operation of the thus-configured observation apparatus 51 will be described.

In order to observe the cells S by using the observation apparatus 51 according to this embodiment, first, for example, the cells S that have been accommodated and cultured in the container 17 in an incubator (not shown) are placed, in the container 17, on the transmission window 4 of the observation apparatus 51. Then, the control portion 15 causes the infrared-light radiating portion 53 to emit the infrared light and to irradiate the medium W in the container 17 therewith, thus heating the medium W. In addition, the thermal camera portion 55 is driven by means of the control portion 15, and the temperature of the medium W is measured by the thermal camera portion 55.

Here, by heating the medium W by means of irradiation with the infrared light, it is possible to efficiently heat the cells S immersed in the medium W. In addition, because there is an extremely high correlation between the temperatures of the medium W and the cells S immersed in the medium W, it is possible to nearly directly measure the temperature of the cells S in the container 17 on the basis of the temperature of the medium W measured by the thermal camera portion 55.

Next, in a state in which the cells S in the container 17 are heated by means of irradiation with the infrared light, the illumination light is emitted from the illumination portion 7, the observation light coming from the cells S is captured by using the camera portion 9, and the obtained image is displayed on the display portion 13. With regard to irradiation of the illumination light and capturing of the observation light, detailed descriptions thereof will be omitted because the procedures thereof are similar to those in the first embodiment. It is also possible to display images of temperature distributions captured by using the thermal camera portion 55 on the display portion 13.

As has been described above, with the observation apparatus 51 according to this embodiment, by acquiring images of the cells S by capturing images thereof while heating the cells S in the container 17 by means of irradiation with the infrared light, it is possible to observe the cells S that have been cultured at an appropriate temperature by using an incubator, while maintaining the state thereof at the appropriate temperature. In this case, it is possible to more accurately ascertain the changes in the temperature of the cells S by more directly measuring the temperature of the cells S by means of the thermal camera portion 55.

This embodiment can be modified as follows.

Figure 13A:
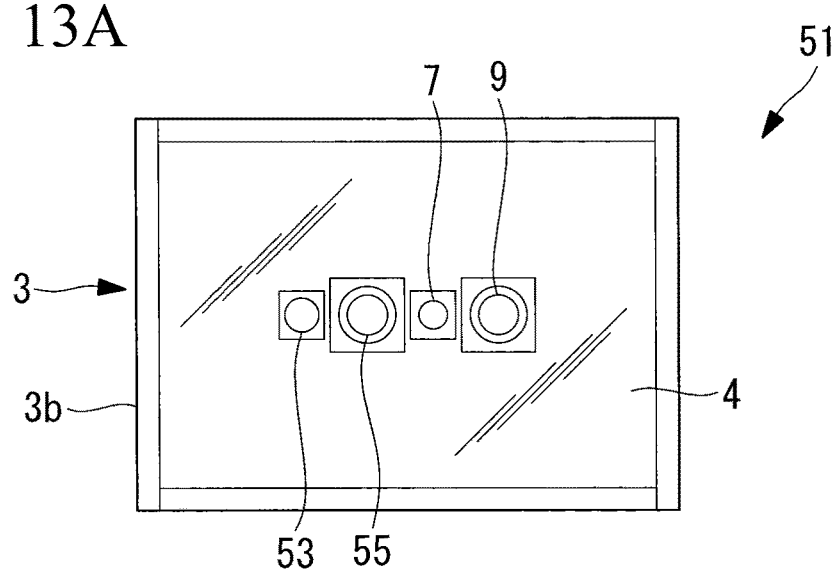
FIG. 13A is a top view showing an observation apparatus according to a first modification of the third embodiment of the present invention as viewed from above.
Figure 13B:
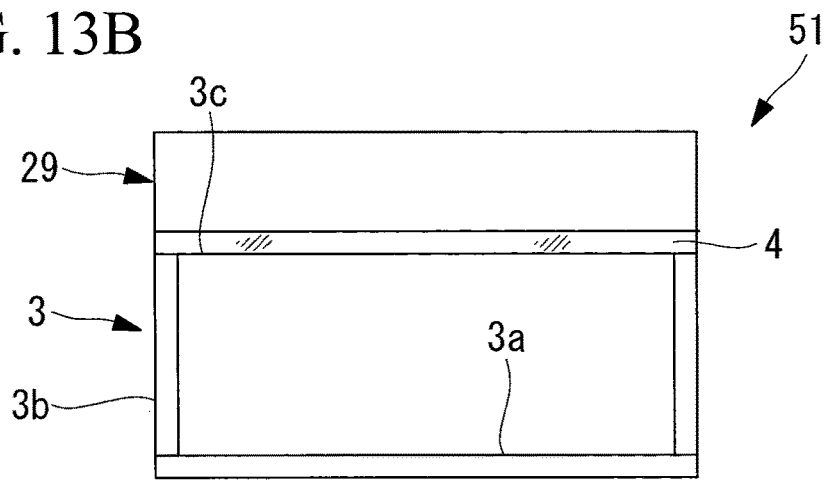
FIG. 13B is a side view in which the observation apparatus in FIG. 13A is viewed from a side.
Figure 13C:
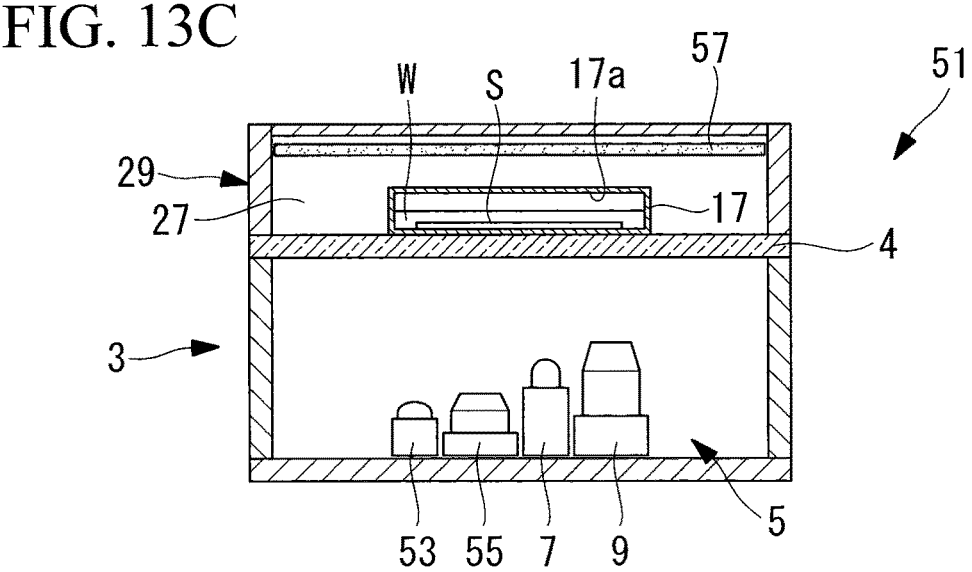
FIG. 13C is a sectional view in which the observation apparatus in FIG. 13B is cut through in the vertical direction.

As a first modification, for example, as shown in FIGS. 13A, 13B, and 13C, it is permissible to provide the opening/closing-type lid portion 29 with which the sealed space 27 can be formed in the peripheral area of the container 17 placed on the transmission window 4 of the housing 3 and a light-absorbing portion 57 that is disposed in the sealed space 27 formed by the lid portion 29 and that absorbs light.

As the light-absorbing portion 57, for example, an aluminum plate painted in matte black may be employed. In addition, the light-absorbing portion 57 may be disposed between the container 17 and the top plate of the lid portion 29 facing the transmission window 4. Note that it is desirable that the light-absorbing portion 57 have gaps between and the side surfaces of the lid portion 29 that surrounds the peripheral area thereof and the light-absorbing portion 57. By doing so, it is possible to enhance the heat resistance of the housing-interior radiation layer 21.

By doing so, with the light-absorbing portion 57, it is possible to block stray light, to temporarily absorb the infrared light that is coming from the infrared-light radiating portion 53 and that has passed through the container 17, and to subsequently radiate, onto the cells S in the container 17, the absorbed light in the form of infrared light again. By doing so, it is possible to reduce nonuniformities in the temperature of the medium W and fogging of the container 17.

Figure 14A:
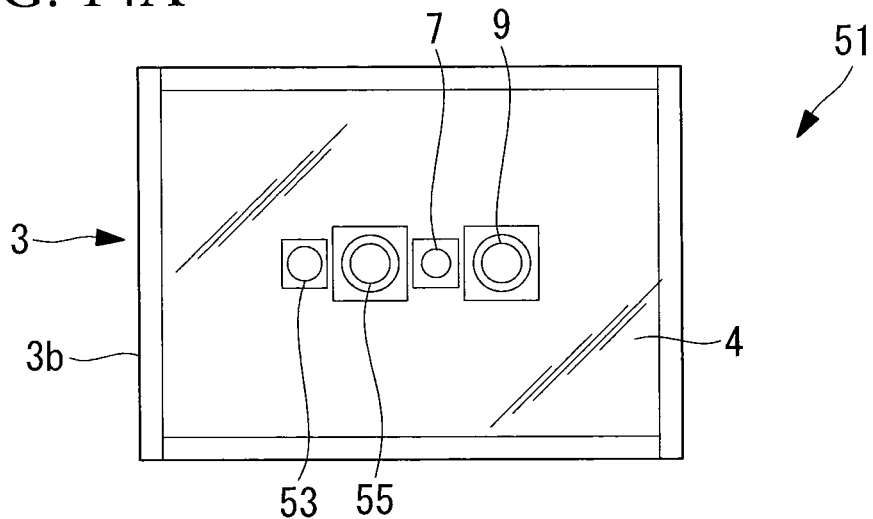
FIG. 14A is a top view showing an observation apparatus according to a second modification of the third embodiment of the present invention as viewed from above.
Figure 14B:
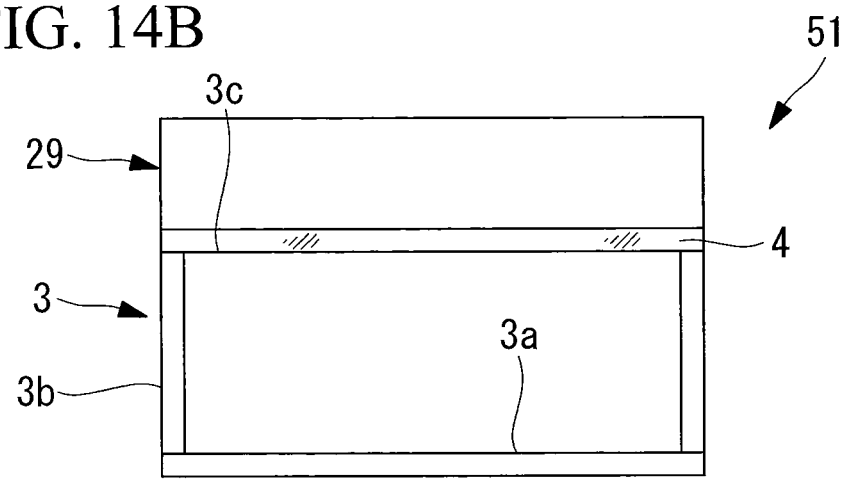
FIG. 14B is a side view in which the observation apparatus in FIG. 14A is viewed from a side.
Figure 14C:
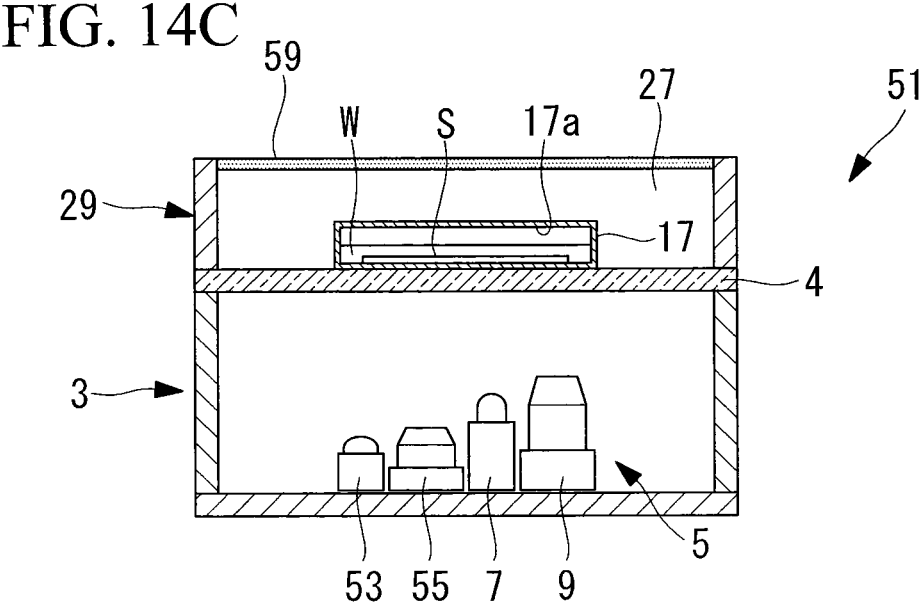
FIG. 14C is a sectional view in which the observation apparatus in FIG. 14B is cut through in the vertical direction.
Figure 15A:
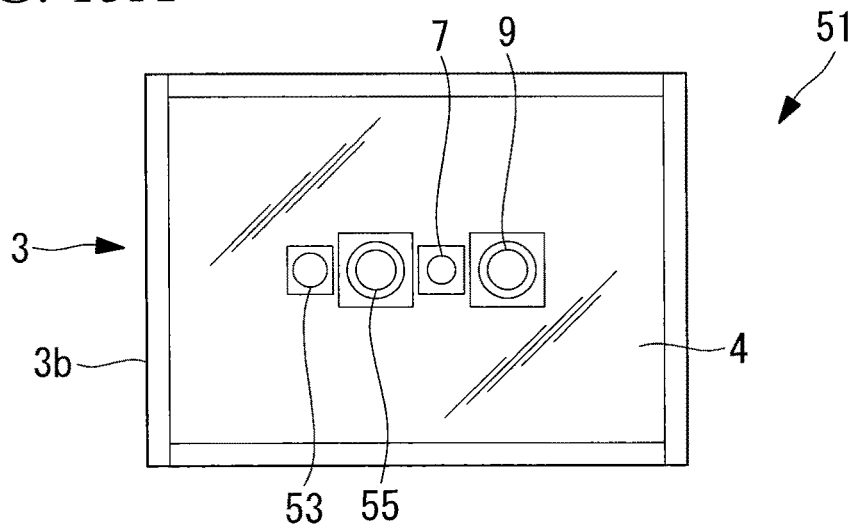
FIG. 15A is a top view showing an observation apparatus according to a third modification of the third embodiment of the present invention as viewed from above.
Figure 15B:
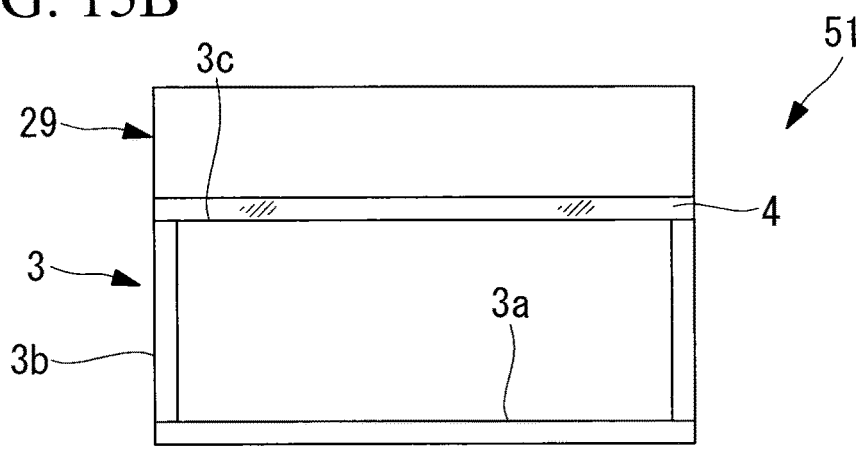
FIG. 15B is a side view in which the observation apparatus in FIG. 15A is viewed from a side.
Figure 15C:
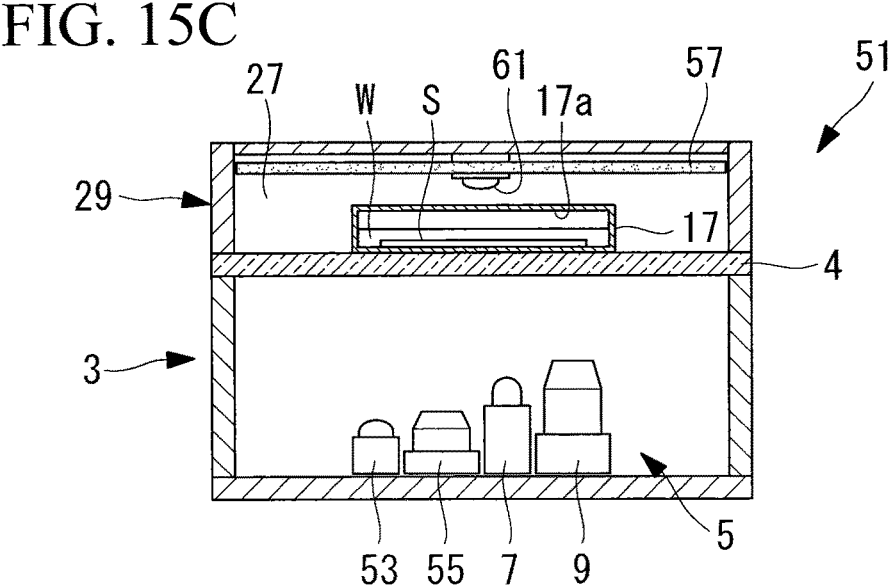
FIG. 15C is a sectional view in which the observation apparatus in FIG. 15B is cut through in the vertical direction.

As a second modification, for example, as shown in FIGS. 14A, 14B, and 14C, it is permissible to provide the opening/closing-type lid portion 29 with which the sealed space 27 can be formed in the peripheral area of the container 17 placed on the transmission window 4 of the housing 3 and a lid-interior reflection layer 59 that reflects the infrared light emitted from the infrared-light radiating portion 53 and the illumination light emitted from the illumination portion 7.

In this case, the top plate of the lid portion 29 facing the transmission window 4 may be configured by using the lid-interior reflection layer 59. As the lid-interior reflection layer 59, for example, a mirror-finished aluminum plate having a high reflectance with respect to infrared light may be employed.

By doing so, the infrared light that is coming from the infrared-light radiating portion 53 and that has passed through the container 17 is reflected and radiated onto the medium W again by means of the lid-interior reflection layer 59, and thus, it is possible to more efficiently heat the medium W. By doing so, by heating the medium W also from above the container 17 by means of reflection, it is possible to reduce the nonuniformities in the temperature and fogging of the container 17.

As a third modification, as shown in FIGS. 15A, 15B, 15C, and 15D, in the configuration of the first modification, an infrared-light radiating portion (lid-interior infrared-light radiating portion) 61 that is disposed on the top plate of the lid portion 29 so as to face the housing 3 may be provided in addition to the infrared-light radiating portion 53 disposed on the bottom face 3a of the housing 3.

The infrared-light radiating portion 61 is configured so as to radiate the infrared light onto the medium W from above the container 17 placed on the transmission window 4. In addition, as with the infrared-light radiating portion 53, the infrared-light radiating portion 61 is configured so as to generate the infrared light at 1450 nm±50 nm or 1940 nm±50 nm.

By doing so, as compared with the case in which only the infrared-light radiating portion 53 is employed, it is possible to more efficiently heat the cells S by radiating the infrared light onto the medium W in the container 17 from two directions, that is, above and below, by using the infrared-light radiating portions 53 and 61.

Fourth Embodiment

Next, an observation apparatus according to a fourth embodiment of the present invention will be described below with reference to the drawings.

As shown in FIGS. 16A, 16B, 16C, and 17, an observation apparatus 63 according to this embodiment differs from that of the third embodiment in that the observation apparatus 63 is provided with the opening/closing-type lid portion 29 with which the sealed space 27 can be formed in the peripheral area of the container 17 placed on the transmission window 4 of the housing 3, and, additionally, structures for externally supplying $CO_2$ and $H_2O$ (vapor) to the sealed space 27 formed by the lid portion 29.

In describing this embodiment, portions having configurations that are the same as those in the observation apparatus 41 according to the second embodiment and the observation apparatus 51 according to the third embodiment, described above, will be given the same reference signs, and descriptions thereof will be omitted.

Figure 16A:
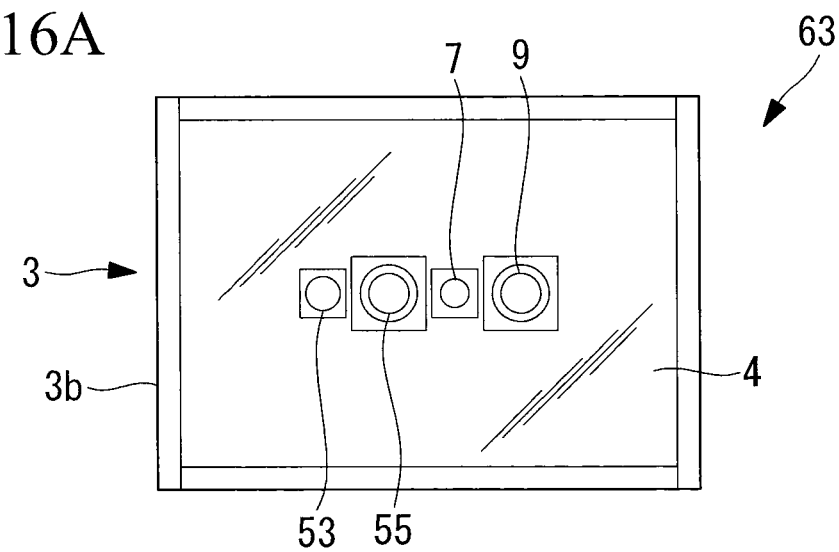
FIG. 16A is a top view showing an observation apparatus according to a fourth embodiment of the present invention as viewed from above.
Figure 16B:
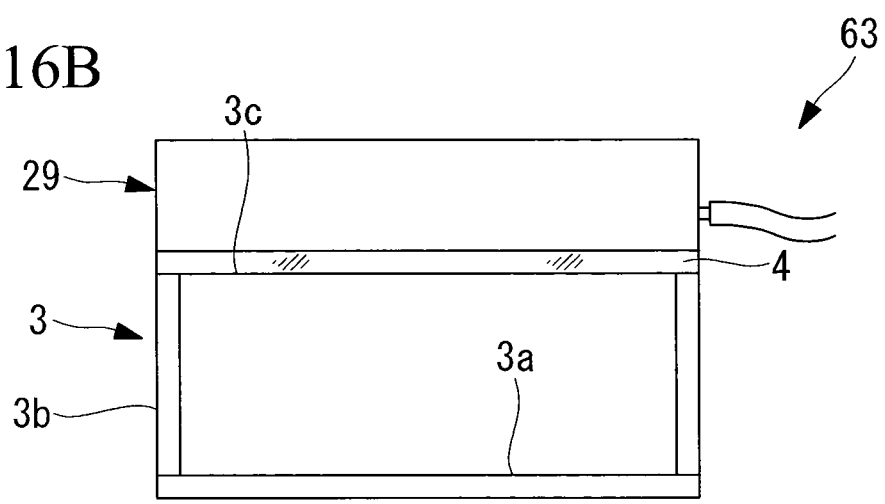
FIG. 16B is a side view in which the observation apparatus in FIG. 16A is viewed from a side.
Figure 16C:
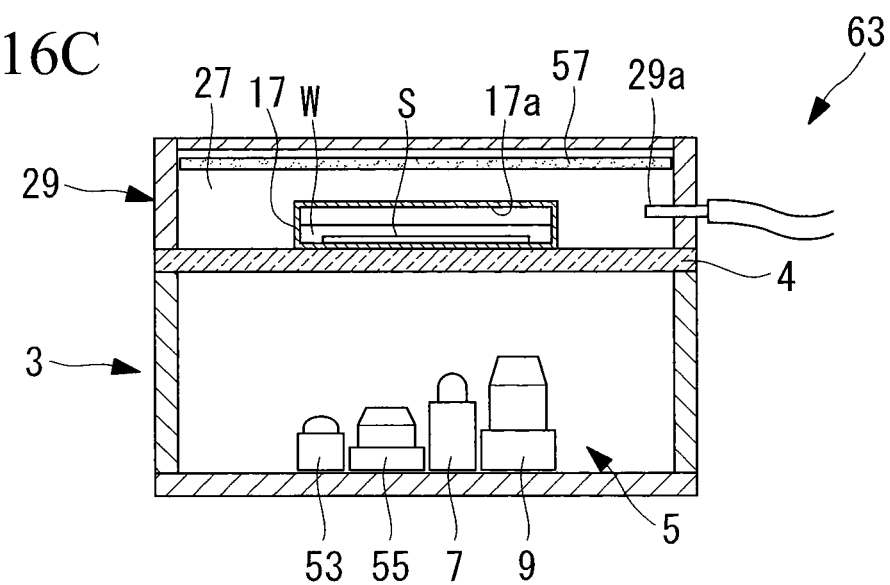
FIG. 16C is a sectional view in which the observation apparatus in FIG. 16C is cut through in the vertical direction.
Figure 17:
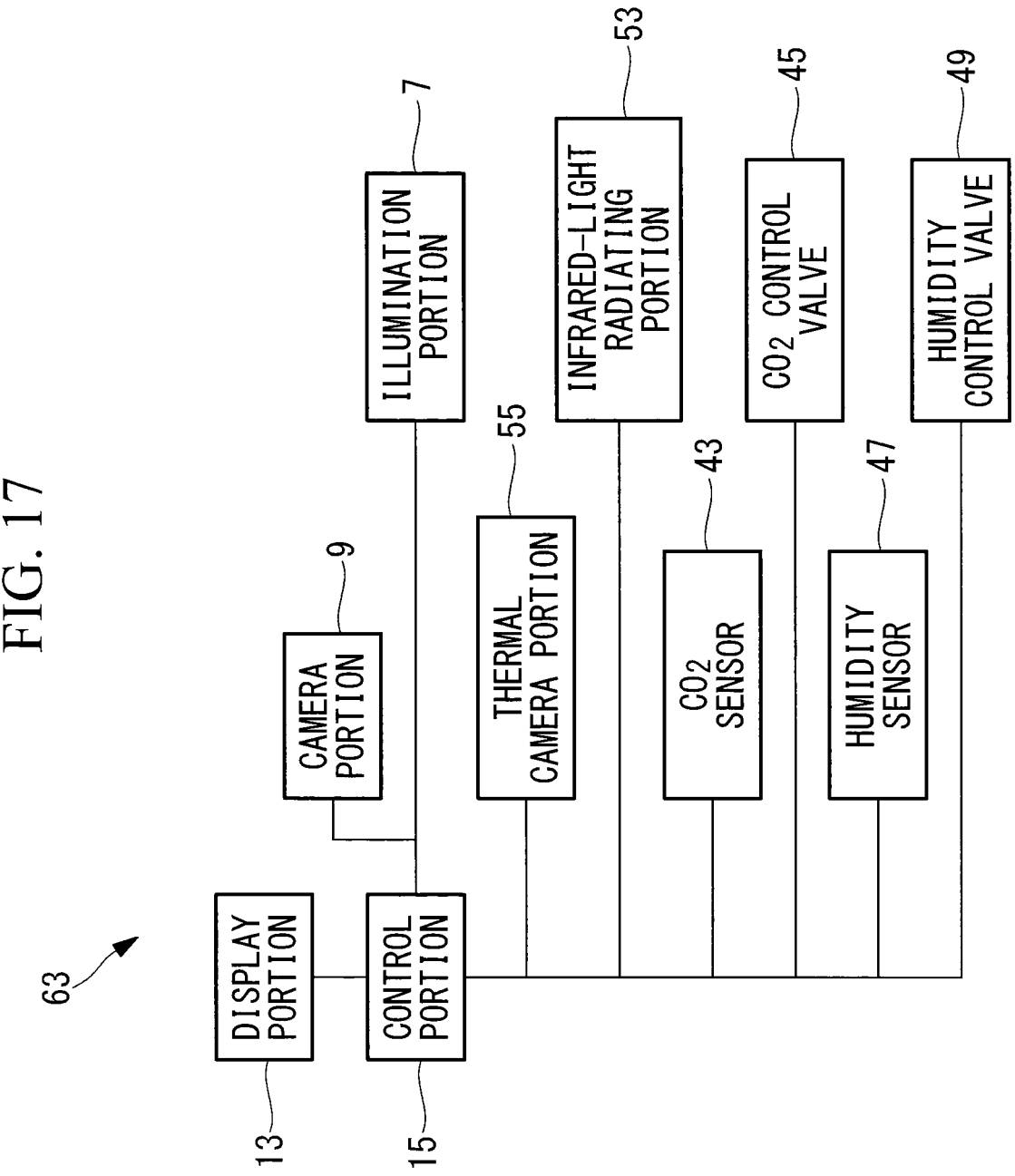
FIG. 17 is a block diagram showing the configuration of the observation apparatus according to the fourth embodiment of the present invention.

As shown in FIG. 16C, the observation apparatus 63 includes the gas supply port 29a in the lid portion 29 as the structure for supplying $CO_2$ and $H_2O$ to the sealed space 27. In addition, as shown in FIG. 17, the observation apparatus 63 is provided with, as the structures for supplying $CO_2$ and $H_2O$ to the sealed space 27: the $CO_2$ storage portion (not shown) that stores $CO_2$, such as a $CO_2$ canister or the like; the $CO_2$ sensor 43; the $CO_2$ control valve 45; the $H_2O$ generating portion (not shown) that generates $H_2O$ (vapor); the humidity sensor 47; and the humidity control valve 49.

With the thus-configured observation apparatus 63, by more directly measuring the temperature of the cells S by means of the thermal camera portion 55 and by managing the $CO_2$ concentration and the humidity in the sealed space 27 by means of the structures for supplying $CO_2$ and $H_2O$ to the sealed space 27, it is possible to observe the cells S while culturing the cells S in a more appropriate environment.

As has been described above, although the embodiments of the present invention have been described in detail with reference to the drawings, specific configurations are not limited to these embodiments, and design alterations or the like within a range that does not depart from the scope of the present invention are also encompassed. For example, the present invention is not limited to forms in which the present invention is applied to the individual embodiments and modifications described above, and the present invention may be applied to embodiments in which these embodiments and modifications are combined, as appropriate, without particular limitation thereto.

From the above-described embodiment, the following invention is derived.

An aspect of the present invention is an observation apparatus including: a housing that has, in a top face thereof, a transmission window on which a container accommodating a sample can be placed and through which light can pass; an image-acquisition portion that is accommodated in the housing and that captures observation light coming from the sample irradiated with illumination light and entering the housing by passing through the transmission window; and a housing-interior heating portion that is accommodated in the housing and that heats the sample.

With this aspect, when the illumination light is radiated onto the sample in the container placed on the transmission window in the top face of the housing, the observation light that is coming from the sample and that has passed through the transmission window enters the housing, and the observation light is captured by the image-acquisition portion in the housing. In this case, by heating the sample by using the heating portion in the housing, it is possible to observe the sample that has been cultured at an appropriate temperature, while maintaining the state thereof at the appropriate temperature.

In the above-described aspect, the housing-interior heating portion may be provided with a resistor that generates radiant heat.

By employing such a configuration, it is possible to uniformly heat the sample by means of the radiant heat emitted from the resistor.

In the above-described aspect, the resistor may be a housing-interior layer-like resistor that is disposed parallel to the transmission window of the housing.

By employing such a configuration, it is possible to efficiently heat the sample over the entire container by means of the housing-interior layer-like resistor that is disposed so as to face the bottom face of the container.

In the above-described aspect, the housing-interior layer-like resistor may be a transparent metal film.

By employing such a configuration, it is possible to capture, by means of the image-acquisition portion, the observation light that is coming from the sample and that has passed through the transmission window by making the observation light pass through the transparent metal film. Therefore, it is not necessary to provide a through-hole in the transparent metal film to allow the observation light to pass therethrough. The transparent metal film may be an ITO film.

In the above-described aspect, the housing-interior heating portion may be provided with a housing-interior radiation layer that is disposed between the transmission window of the housing and the housing-interior layer-like resistor and that makes the radiation of the radiant heat emitted from the housing-interior layer-like resistor uniform.

By employing such a configuration, it is possible to more uniformly heat the sample by causing the radiant heat from the housing-interior layer-like resistor to be uniformly conducted to the sample by means of the housing-interior radiation layer.

In the above-described aspect, the housing-interior heating portion may be provided with a housing-interior reflection layer that is disposed on the opposite side from the transmission window of the housing with the housing-interior layer-like resistor sandwiched therebetween and that reflects the radiant heat emitted from the housing-interior layer-like resistor.

By employing such a configuration, the radiant heat emitted from the housing-interior layer-like resistor in the direction opposite side from the sample is also conducted to the sample by means of the housing-interior reflection layer, and thus, it is possible to more efficiently heat the sample.

The above-described aspect may be provided with a temperature sensor that measures a temperature of the sample.

By employing such a configuration, it is possible to ascertain changes in the temperature of the sample by means of the temperature sensor.

The above-described aspect may be provided with a temperature sensor that measures a temperature of the resistor.

By employing such a configuration, it is possible to ascertain changes in the temperature of the sample without having to directly measure the temperature of the sample. This is effective in the case in which there is a high correlation between the temperature of the sample and the temperature of the resistor.

The above-described aspect may be provided with a lid portion with which a sealed space can be formed in a peripheral area of the container placed on the transmission window of the housing.

By employing such a configuration, by forming the sealed space in the peripheral area of the container by using the lid portion, it is possible to suppress escape of the heat of the sample to the exterior.

The above-described aspect may be provided with a lid-interior heating portion that is disposed in the sealed space and that heats the sample.

By employing such a configuration, it is possible to more efficiently heat the sample by using the lid-interior heating portion in combination with the heating by means of the housing-interior heating portion.

In the above-described aspect, the lid-interior heating portion may be provided with a lid-interior layer-like resistor that is disposed above the container parallel to the transmission window of the housing and that generates radiant heat.

By employing such a configuration, it is possible to efficiently heat the sample over the entire container by means of the lid-interior layer-like resistor that is disposed so as to face the bottom face of the container.

In the above-described aspect, the lid-interior heating portion may be provided with a lid-interior radiation layer that is disposed between the container and the lid-interior layer-like resistor and that makes the radiation of the radiant heat emitted from the lid-interior layer-like resistor uniform.

By employing such a configuration, it is possible to more uniformly heat the sample by causing the radiant heat from the lid-interior layer-like resistor to be uniformly conducted thereto by means of the lid-interior radiation layer.

In the above-described aspect, the lid-interior heating portion may be provided with a lid-interior reflection layer that is disposed above the container and that can reflect the radiant heat toward the container.

By employing such a configuration, the radiant heat conducted above the container is reflected by the lid-interior reflection layer to be radiated onto the sample, and thus, it is possible to more efficiently heat the sample.

In the above-described aspect, the temperature sensor may be a thermal camera that measures a temperature of a medium accommodated in the container.

Because there is a high correlation between the sample temperature and the medium temperature, by employing such a configuration, it is possible to nearly directly measure the temperature of the sample by means of the thermal camera, and thus, it is possible to more accurately ascertain changes in the temperature of the sample.

In the above-described aspect, the housing-interior heating portion may be provided with a housing-interior infrared-light generating portion that generates infrared light at 1450 nm±50 nm or 1940 nm±50 nm.

Because 1450 nm and 1940 nm are the absorption wavelengths of water, by employing such a configuration, in the case in which the sample is immersed in an aqueous medium, it is possible to efficiently heat the sample via the medium by means of the infrared light emitted from the housing-interior infrared-light generating portion.

The above-described aspect may be provided with a lid portion with which a sealed space can be formed in a peripheral area of the container placed on the transmission window of the housing By employing such a configuration, by forming the sealed space in the peripheral area of the container by using the lid portion, it is possible to suppress escape of the heat of the sample to the exterior.

The above-described aspect may be provided with a light-absorbing portion that is disposed in the sealed space and that absorbs light.

By employing such a configuration, in the case in which stray light in the sealed space is blocked and the sample is immersed in an aqueous medium, it is possible to reduce the nonuniformities in the temperature of the medium and fogging of the container.

The above-described aspect may be provided with a lid-interior infrared-light radiating portion that is disposed in the sealed space and that radiates infrared light at 1450 nm±50 nm or 1940 nm±50 nm onto the sample.

By employing such a configuration, in the case in which the sample is immersed in an aqueous medium, it is possible to efficiently heat the sample via the medium by means of the infrared light emitted from the housing-interior infrared-light generating portion and the lid-interior infrared-light radiating portion.

The above-described aspect may be provided with a lid-interior reflection layer that is disposed above the container and that reflects the infrared light emitted from the housing-interior infrared-light generating portion.

By employing such a configuration, it is possible to more efficiently heat the sample by irradiating the sample again with the infrared light by reflecting, by means of the lid-interior reflection layer, the infrared light that is coming from the housing-interior infrared-light generating portion and that has passed through the container.

REFERENCE SIGNS LIST 1, 41, 51, 63 observation apparatus
3 housing
4 transmission window
5 housing-interior heating portion
9 camera portion (image-acquisition portion)
11 temperature sensor
19 housing-interior layer-like resistor (resistor)
21 housing-interior radiation layer
23 housing-interior reflection layer
25 transparent metal film
29 lid portion
31 lid-interior heating portion
33 lid-interior reflection layer
35 lid-interior layer-like resistor
37 lid-interior radiation layer
53 infrared-light radiating portion (housing-interior infrared-light generating portion)
55 thermal camera portion (thermal camera)
57 light-absorbing portion
59 lid-interior reflection layer
61 infrared-light radiating portion (lid-interior infrared-light radiating portion)
S cell (sample)

The invention claimed is:

1. An observation apparatus comprising:
a housing having a transmission window on a face of the housing, the transmission window being configured for light to pass through and to support a container accommodating a sample;
an image sensor accommodated in the housing for capturing an image of the sample irradiated with illumination light, the image sensor capturing the image of the sample through the transmission window; and
a heater accommodated in the housing for heating the sample;
wherein the heater is a housing-interior layer; and
the heater is provided with a housing-interior reflection layer disposed on an opposite side of the transmission window of the housing with the housing-interior layer sandwiched between the transmission window and the housing-interior reflection layer, the housing-interior reflection layer reflecting the radiant heat emitted from the housing-interior layer.

2. The observation apparatus according to claim 1, wherein the heater is provided with a resistor that generates radiant heat.

3. The observation apparatus according to claim 2, wherein the resistor is disposed parallel to the transmission window of the housing.

4. The observation apparatus according to claim 3, wherein the heater is provided with a housing-interior radiation layer that is disposed between the transmission window of the housing and the housing-interior layer resistor, the housing-interior radiation layer making radiation of the radiant heat emitted from the housing-interior layer resistor uniform.

5. The observation apparatus according to claim 1, wherein the housing-interior layer resistor is a transparent metal film.

6. The observation apparatus according to claim 5, wherein the transparent metal film is an ITO film.

7. The observation apparatus according to claim 1, further comprising a temperature sensor that measures a temperature of the sample.

8. The observation apparatus according to claim 7, wherein the temperature sensor comprises a thermal camera that measures a temperature of a medium accommodated in the container.

9. The observation apparatus according to claim 1, further comprising a temperature sensor that measures a temperature of the resistor.

10. The observation apparatus according to claim 1, further comprising a lid positioned on the transmission window of the housing, the lid forming a sealed space in a peripheral area of the container.

11. The observation apparatus according to claim 10, further comprising a lid heater disposed in the sealed space, the lid heater being configured to heat the sample.

12. The observation apparatus according to claim 11, wherein the lid heater is provided with a lid-interior layer resistor disposed on the container parallel to the transmission window of the housing, the lid-interior layer resistor generating radiant heat.

13. The observation apparatus according to claim 12, wherein the lid heater is provided with a lid-interior radiation layer disposed between the container and the lid-interior layer resistor, the lid-interior radiation layer making the radiation of the radiant heat emitted from the lid-interior layer resistor uniform.

14. The observation apparatus according to claim 11, wherein the lid heater is provided with a lid-interior reflection layer disposed above the container such that the lid-interior reflection layer reflecting the radiant heat toward the container.

15. The observation apparatus according to claim 1, wherein the heater is provided with a housing-interior infrared-light generator that generates infrared light at 1450 nm±50 nm or at 1940 nm±50 nm.

16. The observation apparatus according to claim 15, further comprising a lid positioned on the transmission window of the housing, the lid forming a sealed space in a peripheral area of the container.

17. The observation apparatus according to claim 16, further comprising a light-absorbing material disposed in the sealed space, the light-absorbing material absorbing light.

18. The observation apparatus according to claim 16, further comprising a lid heater disposed in the sealed space, the lid heater radiating infrared light at 1450 nm±50 nm or at 1940 nm±50 nm onto the sample.

19. The observation apparatus according to claim 16, further comprising a lid-interior reflection layer disposed on the container, the lid-interior reflection layer reflecting the infrared light emitted from the housing-interior infrared-light generator.

* * * * *